(12) United States Patent
Alvarez et al.

(10) Patent No.: US 12,357,839 B2
(45) Date of Patent: *Jul. 15, 2025

(54) REMOTE MONITORING DEVICES AND RELATED METHODS AND SYSTEMS WITH AUDIBLE AED SIGNAL LISTENING

(71) Applicant: ZOLL Medical Corporation, Chelmsford, MA (US)

(72) Inventors: Adrian A. Alvarez, Huntley, IL (US); Ross G. Krogh, Long Grove, IL (US); Douglas J. Newlin, Wheaton, IL (US)

(73) Assignee: ZOLL Medical Corporation, Chelmsford, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/510,033

(22) Filed: Nov. 15, 2023

(65) Prior Publication Data

US 2024/0157161 A1 May 16, 2024

Related U.S. Application Data

(63) Continuation of application No. 17/491,365, filed on Sep. 30, 2021, now Pat. No. 11,865,352.

(Continued)

(51) Int. Cl.
*A61N 1/39* (2006.01)
*G08B 21/18* (2006.01)
*G08B 25/10* (2006.01)

(52) U.S. Cl.
CPC ......... *A61N 1/3937* (2013.01); *A61N 1/3904* (2017.08); *A61N 1/3925* (2013.01);
(Continued)

(58) Field of Classification Search
CPC .. A61N 1/3937; A61N 1/3904; A61N 1/3925; G08B 21/185; G08B 25/10
See application file for complete search history.

(56) References Cited

U.S. PATENT DOCUMENTS

| 5,348,008 | A | 9/1994 | Bornn et al. |
| 5,562,621 | A | 10/1996 | Claude et al. |

(Continued)

FOREIGN PATENT DOCUMENTS

| CN | 104 548 350 A | 4/2015 |
| WO | WO 2009/034506 A1 | 3/2009 |

(Continued)

OTHER PUBLICATIONS

PCT/US2021/53206, Search Report and Written Opinion dated Jan. 28, 2022, 46 pages.

*Primary Examiner* — John A Tweel, Jr.
(74) *Attorney, Agent, or Firm* — Finch & Maloney PLLC

(57) ABSTRACT

A remote monitoring device and related systems and methods for monitoring and managing by a monitoring service via a communications network a condition of an automated external defibrillator (AED) based on audio signals from the AED. The remote monitoring device includes a housing configured to be positioned outside of the AED such that audio sounds from the AED can be detected. The housing contains at least one processor, a communications module, a first audio sensor, a first audio detection circuitry, a second audio sensor, and a second audio detection circuitry. The communications module is operably connected to the at least one processor and configured to transmit electronic communications to the monitoring service via the communications network. The at least one processor powers on in response to the wakeup notification signal, processes digital audio signals, and transmits a signal to the monitoring service to report a condition of the AED.

25 Claims, 14 Drawing Sheets

Related U.S. Application Data

(60) Provisional application No. 63/085,763, filed on Sep. 30, 2020.

(52) U.S. Cl.
CPC ......... *A61N 1/3968* (2013.01); *A61N 1/3993* (2013.01); *G08B 21/185* (2013.01); *G08B 25/10* (2013.01)

(56) References Cited

U.S. PATENT DOCUMENTS

| | | |
|---|---|---|
| 5,593,426 A | 7/1997 | Morgan et al. |
| 5,650,770 A | 7/1997 | Schlager et al. |
| 5,687,734 A | 11/1997 | Dempsey et al. |
| 5,782,878 A | 7/1998 | Morgan et al. |
| 5,873,040 A | 2/1999 | Dunn et al. |
| 5,891,046 A | 4/1999 | Cyrus et al. |
| 5,891,049 A | 4/1999 | Cyrus et al. |
| 5,929,601 A | 7/1999 | Kaib et al. |
| 5,951,485 A | 9/1999 | Cyrus et al. |
| 5,955,956 A | 9/1999 | Stendahl et al. |
| 5,963,130 A | 10/1999 | Schlager et al. |
| 5,967,975 A | 10/1999 | Ridgeway |
| 5,983,137 A | 11/1999 | Yerkovich |
| 5,987,519 A | 11/1999 | Peifer et al. |
| 6,057,758 A | 5/2000 | Dempsey et al. |
| 6,090,056 A | 7/2000 | Bystrom et al. |
| 6,141,584 A | 10/2000 | Rockwell et al. |
| 6,150,951 A | 11/2000 | Olejniczak |
| 6,198,390 B1 | 3/2001 | Schlager et al. |
| 6,221,010 B1 | 4/2001 | Lucas |
| 6,292,687 B1 | 9/2001 | Lowell et al. |
| 6,301,501 B1 | 10/2001 | Cronin et al. |
| 6,304,780 B1 | 10/2001 | Owen et al. |
| 6,356,192 B1 | 3/2002 | Menard et al. |
| 6,366,919 B2 | 4/2002 | O'Kane, Jr. et al. |
| 6,368,273 B1 | 4/2002 | Brown |
| 6,381,492 B1 | 4/2002 | Rockwell et al. |
| 6,397,104 B1 | 5/2002 | Miller et al. |
| 6,405,083 B1 | 6/2002 | Rockwell et al. |
| 6,427,088 B1 | 7/2002 | Bowman, IV et al. |
| 6,438,417 B1 | 8/2002 | Rockwell et al. |
| 6,493,581 B2 | 12/2002 | Russell |
| 6,518,889 B2 | 2/2003 | Schlager et al. |
| 6,597,948 B1 | 7/2003 | Rockwell et al. |
| 6,599,258 B1 | 7/2003 | Bystrom et al. |
| 6,603,318 B2 | 8/2003 | Hansen et al. |
| 6,694,299 B1 | 2/2004 | Barrer |
| 6,727,814 B2 | 4/2004 | Saltzstein et al. |
| 6,735,473 B2 | 5/2004 | Kolder et al. |
| 6,747,556 B2 | 6/2004 | Medema et al. |
| 6,748,324 B2 | 6/2004 | Patwari et al. |
| 6,759,956 B2 | 7/2004 | Menard et al. |
| 6,775,356 B2 | 8/2004 | Salvucci et al. |
| 6,804,656 B1 | 10/2004 | Rosenfeld et al. |
| 6,871,093 B2 | 3/2005 | Hansen |
| 6,891,469 B2 | 5/2005 | Engellenner |
| 6,926,682 B2 | 8/2005 | Bystrom et al. |
| 6,937,150 B2 | 8/2005 | Medema et al. |
| 6,948,592 B2 | 9/2005 | Kavounas |
| 6,957,102 B2 | 10/2005 | Silver et al. |
| 6,980,112 B2 | 12/2005 | Nee |
| 6,993,386 B2 | 1/2006 | Lin et al. |
| 7,048,185 B2 | 5/2006 | Hart |
| 7,051,236 B2 | 5/2006 | Sanu |
| 7,062,389 B2 | 6/2006 | Johnson et al. |
| 7,088,233 B2 | 8/2006 | Menard |
| 7,091,852 B2 | 8/2006 | Mason et al. |
| 7,110,779 B2 | 9/2006 | Billhartz et al. |
| 7,120,488 B2 | 10/2006 | Nova et al. |
| 7,162,306 B2 | 1/2007 | Caby et al. |
| 7,171,217 B2 | 1/2007 | Beuck |
| 7,231,258 B2 | 6/2007 | Moore et al. |
| 7,245,964 B2 | 7/2007 | Moore et al. |
| 7,251,470 B2 | 7/2007 | Faucher et al. |
| 7,271,704 B2 | 9/2007 | McSheffrey et al. |
| 7,277,752 B2 | 10/2007 | Matos |
| 7,289,029 B2 | 10/2007 | Medema et al. |
| 7,304,573 B2 | 12/2007 | Postma |
| 7,339,468 B2 | 3/2008 | Andres et al. |
| 7,369,968 B2 | 5/2008 | Johnson et al. |
| 7,383,297 B1 | 6/2008 | Atsmon et al. |
| 7,432,813 B2 | 10/2008 | Postma |
| 7,474,218 B2 | 1/2009 | Johnson et al. |
| 7,480,692 B2 | 1/2009 | Atsmon et al. |
| 7,496,532 B2 | 2/2009 | Johnson et al. |
| 7,510,526 B2 | 3/2009 | Merry et al. |
| 7,565,197 B2 | 7/2009 | Haubrich et al. |
| 7,570,994 B2 | 8/2009 | Tamura et al. |
| 7,598,855 B2 | 10/2009 | Scalisi et al. |
| 7,607,014 B2 | 10/2009 | Larson et al. |
| 7,672,720 B2 | 3/2010 | Heath |
| 7,728,715 B2 | 6/2010 | Riedel et al. |
| 7,728,724 B1 | 6/2010 | Scalisi et al. |
| 7,751,971 B2 | 7/2010 | Chang et al. |
| 7,769,465 B2 | 8/2010 | Matos |
| 7,793,850 B1 | 9/2010 | Ho et al. |
| 7,805,190 B2 | 9/2010 | Chapman et al. |
| 7,827,148 B2 | 11/2010 | Mori et al. |
| 7,840,277 B2 | 11/2010 | Matos |
| 7,848,805 B2 | 12/2010 | Ochs et al. |
| 7,877,235 B2 | 1/2011 | McConnell et al. |
| 7,891,435 B2 | 2/2011 | McSheffrey et al. |
| 7,930,023 B2 | 4/2011 | Vaisnys et al. |
| 7,941,480 B2 | 5/2011 | Atsmon et al. |
| 7,953,478 B2 | 5/2011 | Vaisnys et al. |
| 7,957,798 B2 | 6/2011 | Pearce et al. |
| 7,961,089 B2 | 6/2011 | McSheffrey et al. |
| 7,979,136 B2 | 7/2011 | Young et al. |
| 7,991,625 B2 | 8/2011 | Rosenfeld et al. |
| 7,996,081 B2 | 8/2011 | Bystrom et al. |
| 8,009,020 B2 | 8/2011 | Riedel et al. |
| 8,081,071 B1 | 12/2011 | Vaisnys et al. |
| 8,086,320 B2 | 12/2011 | Saketkhou |
| 8,090,439 B2 | 1/2012 | Chapman et al. |
| 8,090,440 B2 | 1/2012 | Chapman et al. |
| 8,090,441 B2 | 1/2012 | Chapman et al. |
| 8,095,403 B2 | 1/2012 | Price |
| 8,116,863 B2 | 2/2012 | Vaisnys et al. |
| 8,121,681 B2 | 2/2012 | Hampton et al. |
| 8,149,112 B2 | 4/2012 | Schlager et al. |
| 8,155,980 B2 | 4/2012 | Parker |
| 8,175,895 B2 | 5/2012 | Rosenfeld et al. |
| 8,185,196 B2 | 5/2012 | Vaisnys et al. |
| 8,185,197 B2 | 5/2012 | Vaisnys et al. |
| 8,185,623 B2 | 5/2012 | Lewis et al. |
| 8,190,730 B2 | 5/2012 | Dempsey |
| 8,207,816 B2 | 6/2012 | Crigger et al. |
| 8,210,047 B2 | 7/2012 | McSheffrey, Jr. et al. |
| 8,224,441 B2 | 7/2012 | Vaisnys et al. |
| 8,224,442 B2 | 7/2012 | Bystrom et al. |
| 8,248,216 B2 | 8/2012 | Riedel et al. |
| 8,258,973 B2 | 9/2012 | Newkirk |
| 8,280,506 B2 | 10/2012 | Vaisnys et al. |
| 8,314,683 B2 | 11/2012 | Pfeffer |
| 8,319,632 B1 | 11/2012 | Vaisnys et al. |
| 8,334,768 B2 | 12/2012 | Eaton et al. |
| 8,344,899 B2 | 1/2013 | Sullivan et al. |
| 8,350,693 B2 | 1/2013 | McSheffrey, Sr. et al. |
| 8,369,266 B2 | 2/2013 | Jin et al. |
| 8,386,035 B2 | 2/2013 | Vaisnys et al. |
| 8,421,605 B2 | 4/2013 | Riedel et al. |
| 8,423,128 B2 | 4/2013 | Goto |
| 8,428,528 B2 | 4/2013 | Sutton et al. |
| 8,433,405 B2 | 4/2013 | Bystrom et al. |
| 8,452,413 B2 | 5/2013 | Young et al. |
| 8,494,628 B2 | 7/2013 | Vaisnys et al. |
| 8,497,774 B2 | 7/2013 | Scalisi et al. |
| 8,498,701 B2 | 7/2013 | Vaisnys et al. |
| 8,526,910 B2 | 9/2013 | Messerly |
| 8,532,764 B2 | 9/2013 | Duke |
| 8,532,766 B2 | 9/2013 | Joo et al. |
| 8,559,913 B2 | 10/2013 | Thijs et al. |

(56) References Cited

U.S. PATENT DOCUMENTS

| | | | |
|---|---|---|---|
| 8,565,871 B2 | 10/2013 | Tuysserkani |
| 8,565,882 B2 | 10/2013 | Matos |
| 8,577,475 B2 | 11/2013 | Bowers |
| 8,600,491 B2 | 12/2013 | McMahon et al. |
| 8,610,557 B2 | 12/2013 | McSheffrey, Sr. et al. |
| 8,666,488 B2 | 3/2014 | Duke |
| 8,669,879 B2 | 3/2014 | Sullivan et al. |
| 8,676,312 B2 | 3/2014 | Daynes et al. |
| 8,682,284 B2 | 3/2014 | Brackett et al. |
| 8,694,100 B2 | 4/2014 | Drew et al. |
| 8,701,495 B2 | 4/2014 | McSheffrey, Jr. et al. |
| 8,737,311 B2 | 5/2014 | Jin et al. |
| 8,738,128 B2 | 5/2014 | Pearce et al. |
| 8,738,129 B2 | 5/2014 | Packer et al. |
| 8,768,441 B2 | 7/2014 | DeZwart et al. |
| 8,774,827 B2 | 7/2014 | Scalisi et al. |
| 8,774,916 B2 | 7/2014 | Vaisnys et al. |
| 8,788,038 B2 | 7/2014 | Neumiller et al. |
| 8,798,743 B1 | 8/2014 | Khoun et al. |
| 8,838,235 B2 | 9/2014 | Cowan et al. |
| 8,854,194 B2 | 10/2014 | McSheffrey et al. |
| 8,868,180 B2 | 10/2014 | Bystrom et al. |
| 8,880,168 B2 | 11/2014 | Pearce et al. |
| 8,890,702 B2 | 11/2014 | Caby et al. |
| 8,920,343 B2 | 12/2014 | Sabatino |
| 8,923,805 B2 | 12/2014 | Single |
| 8,923,960 B2 | 12/2014 | Goto |
| 8,930,040 B2 | 1/2015 | Gompert et al. |
| 8,935,367 B2 | 1/2015 | Atsmon et al. |
| 8,981,927 B2 | 3/2015 | McSheffrey |
| 8,983,378 B2 | 3/2015 | Karuppiah et al. |
| 8,983,607 B2 | 3/2015 | Guo et al. |
| 9,026,147 B2 | 5/2015 | Galvin et al. |
| 9,035,787 B2 | 5/2015 | Bongberg et al. |
| 9,043,217 B2 | 5/2015 | Cashman et al. |
| 9,067,077 B2 | 6/2015 | Drew et al. |
| 9,079,045 B2 | 7/2015 | Cowan et al. |
| 9,082,156 B2 | 7/2015 | Matos |
| 9,092,762 B2 | 7/2015 | Jensen et al. |
| 9,113,473 B2 | 8/2015 | Pixley et al. |
| 9,119,971 B2 | 9/2015 | Elghazzawi |
| 9,138,591 B2 | 9/2015 | Abbenhouse et al. |
| 9,161,692 B2 | 10/2015 | Bowers |
| 9,172,129 B2 | 10/2015 | Szakelyhidi |
| 9,179,866 B2 | 11/2015 | Khoun et al. |
| 9,220,912 B2 | 12/2015 | Elghazzawi |
| 9,230,421 B2 | 1/2016 | Reeder et al. |
| 9,232,040 B2 | 1/2016 | Barash et al. |
| 9,233,256 B2 | 1/2016 | Jorgenson |
| 9,241,666 B2 | 1/2016 | Packer et al. |
| 9,241,867 B2 | 1/2016 | Bystrom et al. |
| 9,265,959 B2 | 2/2016 | Drew et al. |
| 9,289,621 B2 | 3/2016 | Aoyama et al. |
| 9,295,849 B2 | 3/2016 | Elghazzawi et al. |
| 9,311,763 B2 | 4/2016 | Gompert et al. |
| 9,323,893 B2 | 4/2016 | Berry et al. |
| 9,324,120 B2 | 4/2016 | Braun |
| 9,342,976 B2 | 5/2016 | Pfeffer |
| 9,352,109 B2 | 5/2016 | Wittenber et al. |
| 9,364,625 B2 | 6/2016 | Silver et al. |
| 9,364,682 B2 | 6/2016 | Peterson et al. |
| 9,375,584 B2 | 6/2016 | Barnes et al. |
| 9,383,451 B2 | 7/2016 | Johnson |
| 9,415,232 B2 | 8/2016 | Bystrom et al. |
| 9,439,572 B2 | 9/2016 | Pearce et al. |
| 9,451,407 B2 | 9/2016 | van der Laak et al. |
| 10,258,806 B2 | 4/2019 | Elghazzawi et al. |
| 10,298,072 B2 | 5/2019 | Stever et al. |
| 10,871,379 B2 | 12/2020 | Johnson |
| 11,103,719 B2 | 8/2021 | Halsne |
| 11,122,394 B2 | 9/2021 | Stapleford |
| 11,185,708 B2 * | 11/2021 | Hochhalter ......... A61N 1/3904 |
| 11,207,535 B2 | 12/2021 | Halsne |
| 11,478,655 B2 | 10/2022 | Beattie |
| 11,865,352 B2 * | 1/2024 | Alvarez ............ A61N 1/3993 |
| 2003/0025602 A1 | 2/2003 | Medema et al. |
| 2003/0028219 A1 | 2/2003 | Powers et al. |
| 2003/0065536 A1 | 4/2003 | Hansen et al. |
| 2003/0069648 A1 | 4/2003 | Douglas et al. |
| 2003/0212438 A1 | 11/2003 | Nova et al. |
| 2004/0019258 A1 | 1/2004 | Kavounas et al. |
| 2004/0027245 A1 | 2/2004 | Schlager et al. |
| 2004/0049233 A1 | 3/2004 | Edwards |
| 2004/0128178 A1 | 7/2004 | Barrer |
| 2004/0172069 A1 | 9/2004 | Hakala |
| 2005/0148887 A1 | 7/2005 | Reiter et al. |
| 2006/0030891 A1 | 2/2006 | Saltzstein et al. |
| 2006/0092029 A1 | 5/2006 | Browne et al. |
| 2006/0142808 A1 | 6/2006 | Pearce et al. |
| 2006/0149321 A1 | 7/2006 | Merry et al. |
| 2006/0149322 A1 | 7/2006 | Merry et al. |
| 2006/0247963 A1 | 11/2006 | Barrer et al. |
| 2006/0287586 A1 | 12/2006 | Murphy |
| 2007/0032830 A1 | 2/2007 | Bowers |
| 2007/0090355 A1 | 4/2007 | Solosko et al. |
| 2007/0162075 A1 | 7/2007 | O'Hara |
| 2007/0174438 A9 | 7/2007 | Johnson et al. |
| 2007/0185545 A1 | 8/2007 | Duke |
| 2007/0229350 A1 | 10/2007 | Scalisi et al. |
| 2007/0270909 A1 | 11/2007 | Saketkhou |
| 2008/0140140 A1 | 6/2008 | Grimley et al. |
| 2008/0177341 A1 | 7/2008 | Bowers |
| 2008/0250166 A1 | 10/2008 | Edwards |
| 2009/0112274 A1 | 4/2009 | Herbert |
| 2009/0149894 A1 | 6/2009 | Merry et al. |
| 2009/0264948 A1 | 10/2009 | Tamura et al. |
| 2010/0023074 A1 | 1/2010 | Powers et al. |
| 2011/0205031 A1 | 8/2011 | Wakabayashi et al. |
| 2011/0295078 A1 | 12/2011 | Reid et al. |
| 2012/0112903 A1 | 5/2012 | Kaib et al. |
| 2012/0123490 A1 | 5/2012 | Daynes et al. |
| 2012/0123504 A1 | 5/2012 | Daynes et al. |
| 2012/0191476 A1 | 7/2012 | Reid et al. |
| 2012/0197665 A1 | 8/2012 | Lewis et al. |
| 2012/0271370 A1 | 10/2012 | Hochhalter et al. |
| 2013/0012151 A1 | 1/2013 | Hankins |
| 2013/0053063 A1 | 2/2013 | McSheffrey |
| 2013/0087609 A1 | 4/2013 | Nichol et al. |
| 2013/0096649 A1 | 4/2013 | Martin et al. |
| 2013/0132465 A1 | 5/2013 | Brown |
| 2013/0304142 A1 | 11/2013 | Curtin et al. |
| 2013/0304143 A1 | 11/2013 | Banville |
| 2013/0304145 A1 | 11/2013 | Aoyama et al. |
| 2013/0304146 A1 | 11/2013 | Aoyama et al. |
| 2014/0002241 A1 | 1/2014 | Elghazzawi |
| 2014/0004814 A1 | 1/2014 | Elghazzawi |
| 2014/0005506 A1 | 1/2014 | Elghazzawi |
| 2014/0025129 A1 | 1/2014 | Abbenhouse et al. |
| 2014/0043149 A1 | 2/2014 | Cowan et al. |
| 2014/0142647 A1 | 5/2014 | McMahon et al. |
| 2014/0207371 A1 | 7/2014 | Johnson |
| 2014/0236615 A1 | 8/2014 | Ragusky et al. |
| 2014/0243036 A1 | 8/2014 | Kouwe |
| 2014/0272860 A1 | 9/2014 | Peterson et al. |
| 2014/0277227 A1 | 9/2014 | Peterson et al. |
| 2014/0278463 A1 | 9/2014 | Merry et al. |
| 2014/0292534 A1 | 10/2014 | Stever et al. |
| 2014/0303507 A1 | 10/2014 | Neumiller et al. |
| 2015/0018894 A1 | 1/2015 | Pearce et al. |
| 2015/0046175 A1 | 2/2015 | Jorgenson et al. |
| 2015/0067021 A1 | 3/2015 | Protas et al. |
| 2015/0087920 A1 | 3/2015 | Johnson et al. |
| 2015/0088016 A1 | 3/2015 | Fleischacker et al. |
| 2015/0109125 A1 | 4/2015 | Kaib et al. |
| 2015/0112400 A1 | 4/2015 | An |
| 2015/0112704 A1 | 4/2015 | Braun |
| 2015/0213212 A1 | 7/2015 | Grimley et al. |
| 2015/0227694 A1 | 8/2015 | Grimley |
| 2015/0265844 A1 | 9/2015 | Powers et al. |
| 2015/0297906 A1 | 10/2015 | Guichet |
| 2015/0306409 A1 | 10/2015 | Greiner et al. |
| 2015/0321020 A1 | 11/2015 | Gumbrell |
| 2015/0335244 A1 | 11/2015 | Guiney et al. |
| 2015/0343227 A1 | 12/2015 | Elghazzawi |

(56) References Cited

U.S. PATENT DOCUMENTS

| | | | |
|---|---|---|---|
| 2016/0020505 A1 | 1/2016 | Szakelyhidi |
| 2016/0023007 A1 | 1/2016 | Stouffer et al. |
| 2016/0023009 A1 | 1/2016 | Elghazzawi |
| 2016/0034644 A1 | 2/2016 | Guiney et al. |
| 2016/0058996 A1 | 3/2016 | Hoss et al. |
| 2016/0095529 A1 | 4/2016 | Khoun et al. |
| 2016/0100302 A1 | 4/2016 | Barash et al. |
| 2016/0106362 A1 | 4/2016 | Packer et al. |
| 2016/0133160 A1 | 5/2016 | Packer et al. |
| 2016/0148495 A1 | 5/2016 | Buchanan |
| 2016/0154942 A1 | 6/2016 | Delisle et al. |
| 2016/0158527 A1 | 6/2016 | Jensen et al. |
| 2016/0166149 A1 | 6/2016 | Bowers |
| 2016/0166349 A1 | 6/2016 | Guichet |
| 2016/0166839 A1 | 6/2016 | Drew et al. |
| 2016/0175602 A1 | 6/2016 | Aoyama et al. |
| 2016/0180044 A1 | 6/2016 | Delisle et al. |
| 2016/0184598 A1 | 6/2016 | Delisle et al. |
| 2016/0193109 A1 | 7/2016 | Fleischacker et al. |
| 2016/0193474 A1 | 7/2016 | Gumbrell |
| 2016/0206839 A1 | 7/2016 | Freeman et al. |
| 2016/0213942 A1 | 7/2016 | Elghazzawi et al. |
| 2016/0225289 A1 | 8/2016 | Ehinger et al. |
| 2016/0270738 A1 | 9/2016 | Volpe et al. |
| 2017/0003356 A1 | 1/2017 | Kaib et al. |
| 2019/0015672 A1 | 1/2019 | Halsne |
| 2019/0060657 A1 | 2/2019 | Halsne |
| 2019/0111272 A1 | 4/2019 | Hochhalter |
| 2020/0054884 A1 | 2/2020 | Aprile |

FOREIGN PATENT DOCUMENTS

| | | |
|---|---|---|
| WO | WO 2012/017354 A2 | 2/2012 |
| WO | 2012/057868 A1 | 5/2012 |
| WO | WO 2012/064547 A1 | 5/2012 |
| WO | WO 2012/064604 A1 | 5/2012 |
| WO | WO 2012/100219 A1 | 7/2012 |
| WO | WO 2013/056194 A1 | 4/2013 |
| WO | WO 2013/128308 A1 | 9/2013 |
| WO | WO 2013/128315 A2 | 9/2013 |
| WO | WO 2013/128327 A1 | 9/2013 |
| WO | WO 2013/128340 A1 | 9/2013 |
| WO | WO 2013/169294 A1 | 11/2013 |
| WO | WO 2013/169295 A1 | 11/2013 |
| WO | WO 2013/169296 A1 | 11/2013 |
| WO | WO 2013/169297 A1 | 11/2013 |
| WO | WO 2014/024081 A2 | 2/2014 |
| WO | WO 2014/024096 A1 | 2/2014 |
| WO | WO 2014/097035 A1 | 6/2014 |
| WO | WO 2014/102726 A1 | 7/2014 |
| WO | WO 2014/160838 A1 | 10/2014 |
| WO | WO 2014/207630 A1 | 12/2014 |
| WO | WO 2015/013680 A1 | 1/2015 |
| WO | WO 2015/022618 A1 | 2/2015 |
| WO | WO 2015/048528 A2 | 4/2015 |
| WO | WO 2015/063650 A1 | 5/2015 |
| WO | WO 2015/145272 A1 | 10/2015 |
| WO | WO 2016/097982 A1 | 6/2016 |
| WO | WO 2016/108132 A1 | 7/2016 |
| WO | 2017/162627 A1 | 9/2017 |
| WO | 2018/009377 A1 | 1/2018 |
| WO | WO 2019/092443 A1 | 5/2019 |
| WO | WO 2019/112844 A1 | 6/2019 |

\* cited by examiner

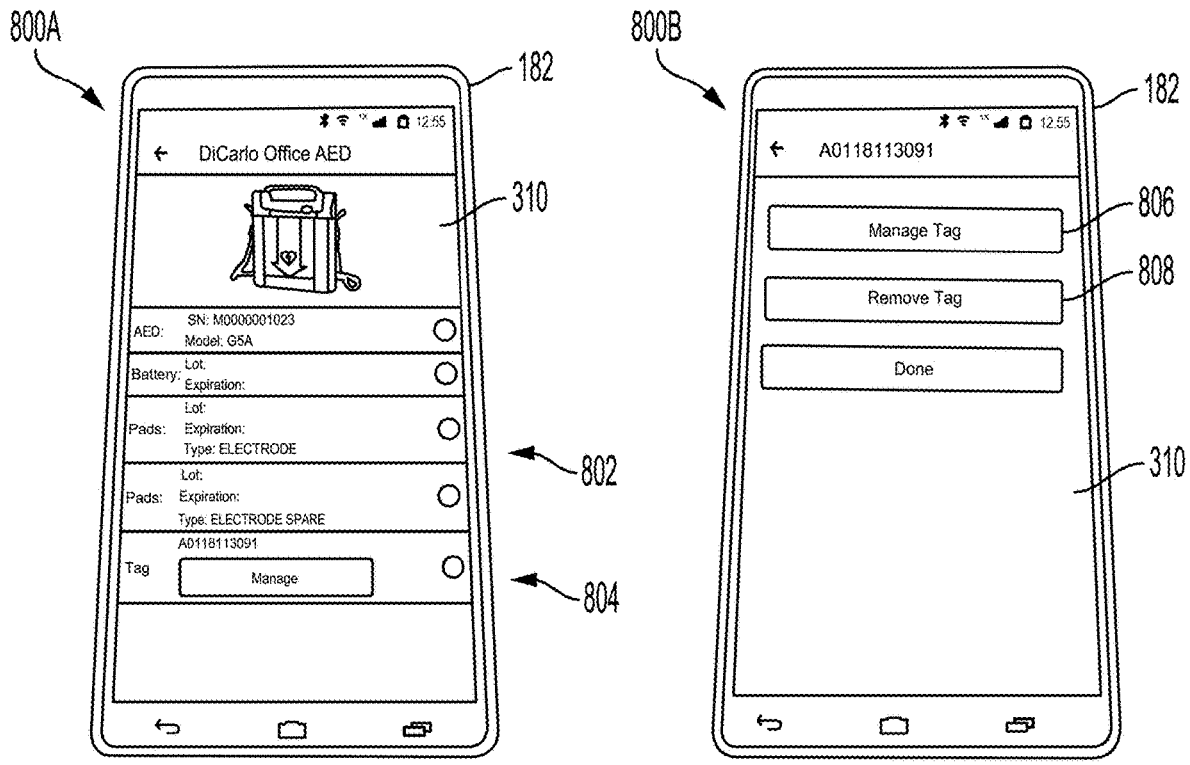
FIG. 11A
FIG. 11B
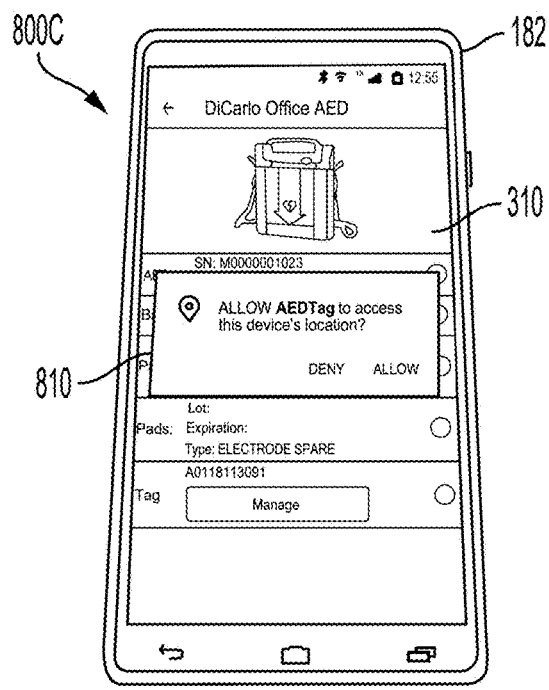
FIG. 11C

REMOTE MONITORING DEVICES AND RELATED METHODS AND SYSTEMS WITH AUDIBLE AED SIGNAL LISTENING

CROSS REFERENCE TO RELATED APPLICATIONS

This application claims the benefit under 35 U.S.C. § 120 as a continuation of U.S. patent application Ser. No. 17/491,365, filed Sep. 30, 2021, titled "REMOTE MONITORING DEVICES AND RELATED METHODS AND SYSTEMS WITH AUDIBLE AED SIGNAL LISTENING," which claims the benefit under 35 U.S.C. 119(e) to U.S. Provisional Application No. 63/085,763, filed Sep. 30, 2020, which are hereby incorporated herein by reference in their entireties for all purposes.

TECHNICAL FIELD

This disclosure relates to remote monitoring and management of one or more Automated External Defibrillator(s) (AED), for example, by remote monitoring devices located in the proximity of an existing AED that listen to audio signals from the AED and relay condition information via a communications network and related methods and systems.

BACKGROUND

Remotely deployed AEDs, especially those located in homes, offices, and public spaces, require monitoring to ensure peak performance and readiness for use. These types of devices, however, usually lack continual and frequent monitoring for proper maintenance by trained technical specialists. This is especially true of publicly accessible AEDs which are not located in hospitals or health care institutions. Publicly accessible AEDs are required to be dependable devices ready for rapid use by untrained members of the general public such that the AEDs are ready to use without servicing or maintenance during an emergency.

Some past approaches to addressing AED monitoring involve augmenting AEDs themselves with an embedded means of bi-directional, wireless communication for sending and receiving useful monitoring data. However, AEDs with embedded bi-directional wireless communications can require owners and manufacturers to expend a substantial amount of specialized and financial resources to monitor, augment and defend against threats. Moreover, the large number of AEDs already in service would need replacement for this type of monitoring. Such efforts can be costly in their development and execution and can delay other AED improvements.

Other approaches to AED monitoring have been suggested that involve AED monitoring stations or devices. However, many of these have limitations or undesirable configurations for listening structures, device testing, provisioning, or overall system design and integration which could use improvements. AED devices may be installed in a wide variety of locations with a wide range of supporting infrastructure as well as ambient conditions. Monitoring devices that require installation and/or connection to power and communication systems are thus not well-suited for such a wide range of installation environments. Likewise, the wide range of ambient conditions in which AED devices may be installed complicates the monitoring environment for both visual and audio monitoring of such devices and increases the problems for consistent and reliable remote monitoring of such devices.

Accordingly, remote monitoring devices, systems or methods enabling effective remote collection of AED condition information that can be relayed via a communications network across a wide range of installation and monitoring environments for both new and existing AED devices are desired.

SUMMARY

Embodiments described or otherwise contemplated herein substantially provide the advantages of improved devices, systems, and methods that enable enhanced remote monitoring and management of one or more AEDs. Accordingly, proper maintenance and readiness of AEDs is made possible across a wide range of installation and monitoring environments for both new and existing AED devices.

An embodiment relates to a remote monitoring device for monitoring and managing by a monitoring service via a communications network a condition of an AED based on audio signals from the AED. The remote monitoring device includes a housing configured to be positioned outside of the AED such that audio sounds from the AED can be detected. The housing contains at least one processor, a communications module, a first audio sensor, a first audio detection circuitry, a second audio sensor, and a second audio detection circuitry. The communications module is operably connected to the at least one processor and configured to transmit electronic communications to the monitoring service via the communications network. The first audio detection circuitry is operably connected to the first audio sensor and the at least one processor. The first audio detection circuitry is configured to generate a wakeup notification signal when the first audio detection circuitry detects audio sounds during a predetermined detection interval. The second audio detection circuitry is operably connected to the second audio sensor and the at least one processor. The second audio detection circuitry is configured to power on in response to the wakeup notification signal and commence an active listening mode to provide digital audio signals to the at least one processor. The at least one processor is configured to power on in response to the wakeup notification signal, process the digital audio signals, and transmit a signal to the monitoring service to report a condition of the AED based on the digital audio signals that are processed.

An embodiment relates to a remote monitoring device for monitoring audio signals from an AED and electronically reporting to a monitoring service via a communications network. The remote monitoring device includes a housing configured to be positioned outside of the AED such that audio sounds from the AED can be detected. The housing contains a communications module, a first audio sensor, a first audio detection circuitry, a second audio sensor, a second audio detection circuitry, and at least one processor. The communications module is configured to transmit electronic communications to the monitoring service via the communications network. The first audio detection circuitry is operably coupled with the first audio sensor. The first audio detection circuitry is configured to detect audio sounds from the AED via the first audio sensor. The second audio detection circuitry is operably coupled with the second audio sensor, the second audio detection circuitry configured to detect the audio sounds from the AED via the second audio sensor. The at least one processor is operably coupled with the communications module, the first audio detection circuitry, and the second audio detection circuitry. The at least one processor configured to: power on the first audio detection circuitry during a periodic detection interval to detect the audio sounds during the periodic detection interval; process signals from the first audio detection circuitry and generate a wakeup notification signal in response to the detected audio sounds during the periodic detection interval; activate the second audio detection circuitry to commence an active listening mode in response to the generated wakeup notification signal; process signals from the second audio detection circuitry during the active listening mode to make a determination that the AED is in need of service; and transmit a report signal to the monitoring service based on the determination that the AED is in need of service.

An embodiment relates to a remote monitoring device for monitoring audio signals from an AED and electronically reporting to a monitoring service via a communications network. The remote monitoring device includes a housing configured to be positioned outside of the AED such that audio signals from the AED can be detected. The housing contains a communications module, at least one audio sensor, at least one audio detection circuitry, and at least one processor. The communications module is configured to transmit electronic communications to the monitoring service via the communications network. The at least one audio detection circuitry is operably coupled with the at least one audio sensor. The at least one audio detection circuitry is configured to detect audio sounds from the AED via the at least one audio sensor. The at least one processor is operably coupled with the communications module and the at least one audio detection circuitry. The at least one processor is configured to: process signals from the at least one audio detection circuitry based on the detected audio sounds; detect a first audio signal from the processed signals; in response to the first audio signal being detected, commence an active listening mode to detect a second audio signal from the processed signals and confirm that the second audio signal meets a predetermined criterion associated with the active listening mode; in response to the second audio signal being detected, re-commence the active listening mode to detect a third audio signal from the processed signals and confirm that the third audio signal meets the predetermined criterion associated with the active listening mode; and transmit a report signal to the monitoring service if the third audio signal meets the predetermined criterion.

An embodiment relates to a remote monitoring device for monitoring audio signals from an AED and electronically reporting to a monitoring service via a communications network. The remote monitoring device includes a housing configured to be positioned outside of the AED such that audio signals from the AED can be detected. The housing contains at least one processor, a communications module, a first audio sensor, a first audio detection circuitry, a second audio sensor, and a second audio detection circuitry. The communications module is operably connected to the at least one processor and is configured to transmit electronic communications to the monitoring service via the communications network. The first audio detection circuitry is operably connected to the first audio sensor and the at least one processor. The second audio detection circuitry is operably connected to the second audio sensor and the at least one processor. The at least one processor is configured to: reside in a low power sleep state by default; commence a detection state for wakeup confirmation during a detection interval in which the first audio detection circuitry is configured to power on and generate a wakeup notification signal when the first audio detection circuitry detects audio sounds during the detection interval via the first audio sensor; commence a listening state for alert confirmation in response to the wakeup notification signal in which the second audio detection circuitry is configured to power on and provide digital audio signals to the at least one processor in an active listening mode; and commence a transmission state, upon confirmation of at least three consecutive qualifying tones in the audio signals detected in corresponding qualifying intervals during the digital listening state, in which the communications module is caused to transmit a message to the monitoring service via the communications network indicating a status of the AED.

An embodiment relates to a remote monitoring device for monitoring audio signals from an AED and electronically reporting to a monitoring service via a communications network. The remote monitoring device includes a housing configured to be positioned outside of the AED but in a close proximity such that audio signals and personal area network (PAN) wireless signals from the AED can be detected. The housing contains at least one processor, a communications module, a first audio sensor, audio detection circuitry and PAN wireless circuitry for short-range PAN communication protocols such as the Internet of Things (TOT) or Bluetooth Low Energy (BTLE) or Near Field Communications (NFC). The communications module is operably connected to at least one processor and is configured to transmit electronic communications to the monitoring service via the communications network via one or more of a local area network (LAN) Internet connection such as WiFi, or a wide area network (WAN) Internet/telephone connection as a cellular connection, such as 3G, 4G or 5G communication protocols, or a satellite Internet connection such as Low Earth Orbit (LEO) SIM cards. In various embodiments, the at least one processor is configured to: reside in a low power sleep state by default; commence a detection state for wakeup confirmation during a detection interval in which the audio detection circuitry is configured to power on and generate a wakeup notification signal when the audio detection circuitry detects audio sounds during the detection interval. In response to the wakeup notification signal, the at least one processor is configured to receive and analyze at least one of audible sounds and/or short-range wireless communications from the AED, and the communications module is then selectively caused to transmit a message to the monitoring service via the communications network indicating a status, a parameter and/or a change in a status or a parameter of the AED or of the communication link between the AED and the remote monitoring device. In one embodiment, the audio detection circuitry includes a first audio detection circuitry, a second audio sensor, and a second audio detection circuitry wherein a wakeup notification signal is generated when a first audio detection circuitry detects audio sounds during the detection interval via the first audio sensor; commence a listening state for alert confirmation in response to the wakeup notification signal in which the second audio detection circuitry is configured to power on and provide digital audio signals to the at least one processor in an active listening mode; and commence a transmission state, upon confirmation of at least three consecutive qualifying tones in the audio signals detected in corresponding qualifying intervals during the digital listening state, in which the communications module is caused to transmit a message to the monitoring service via the communications network. In some embodiments, the digital listening state can monitor audible signals from the AED, one-way short-range PAN wireless signals from the AED, or a combination of both, including in various embodiments configured to monitor both signals for confirmation and/or verification of one or both of wakeup signals or status signals to reduce false positive alerts.

In some embodiments, the communications module includes switching circuitry configured to selectively switch among two or more of the Internet connection, cellular connection and/or satellite connection. In various embodiments, the switching circuit may be activated by commands from the mobile app or by the remote monitoring device in response to detection of a communication issue between the communications model and the monitoring service via the communication network.

In some embodiments, a location of the remote monitoring device may be determined from cellular location triangulation and/or an optional GPS circuit. In such embodiments, the location determination of the remote monitoring device enables initial programming and setup of pairs of AEDs and corresponding remote monitoring devices in a central location before deployment of the pairs of an AED and a corresponding remote monitoring device to different physical locations in a facility or campus.

In some embodiments, the remote monitoring device further includes a physical indicator, such as a low-power LED indicator, of the status of the communication link between the AED and the remote monitoring device, wherein the status of the communication link may be indicated in response to a proximity detection between the AED and the remote monitoring device.

An embodiment relates to a remote monitoring device for monitoring audio signals from an AED and electronically reporting to a monitoring service via a communications network. The remote monitoring device includes a housing configured to be positioned outside of the AED such that audio signals from the AED can be detected. The housing contains at least one processor, a memory, a communications module, a speaker, at least one audio sensor, and at least one audio detection circuitry. The memory is operably connected to the at least one processor. The communications module is operably connected to the at least one processor and configured to transmit electronic communications to the monitoring service via the communications network. The speaker is operably connected to the at least one processor and configured to generate audio sounds as part of a self-test of the remote monitoring device. The at least one audio detection circuitry is operably coupled with the at least one audio sensor. The at least one audio detection circuitry is configured to detect audio sounds via the at least one audio sensor and provide digital audio signals to the at least one processor. The at least one processor is configured to: periodically cause the speaker to generate the audio sounds as part of the self-test of the remote monitoring device; receive the digital audio signals to confirm that the audio sounds as part of the self-test of the remote monitoring device originate from the speaker; and transmit a message conveying results of the self-test of the remote monitoring device to the monitoring service via the communications network.

An embodiment relates to a system for AED monitoring utilizing a mobile device. The system includes a mobile application and a remote management server. The mobile application is configured to be executable on the mobile device to receive data about an AED and an AED remote monitoring device. The remote management server is configured to communicate with the mobile device and receive data from the mobile device. The mobile application executable on the mobile device is configured to: establish a communications connection between the mobile device and the AED remote monitoring device; establish a communications connection between the mobile device and the remote management server; receive a location of at least one of the AED or the AED remote monitoring device; use the communications connection between the mobile device and the AED remote monitoring device and the location to configure the AED remote monitoring device with site-specific parameters; and communicate a notification to the remote management server of an attempt of the AED remote monitoring device to connect to the remote management server.

An embodiment relates to a method for AED monitoring utilizing a mobile device. The method includes establishing, by a mobile application configured to be executable on a mobile device, a communication connection between the mobile device and the AED remote monitoring device. The method includes establishing, by the mobile application, a communications connection between the mobile device and a remote management server that is configured to communicate with the mobile application and receive data from the mobile device. The method includes launching, by the remote management server, an AED kit engine upon determining that a mobile application is activated on the mobile device. The method includes executing, by the remote management server, the AED kit engine to establish an AED kit that pairs the AED and the AED remote monitoring device and includes at least product data about the AED and the AED monitoring device. The method includes receiving, via at least one of the mobile application or the remote management server, an AED kit location. The method includes configuring, via at least one of the mobile application or the remote management server, the AED remote monitoring device with site-specific parameters using the communications connection. The method includes communicating, via at least one of the mobile application or the remote management server, a notification of an attempt of the AED remote monitoring device to connect to the remote management server.

An embodiment relates to a system for AED monitoring utilizing a mobile device. The system includes a mobile application and a remote management server. The mobile application is configured to be executable on the mobile device to receive identification data about an AED and an AED remote monitoring device. The remote management server is configured to communicate with the mobile device and receive data from the mobile device. The mobile application is executable on the mobile device is configured to: establish a communications connection between the mobile device and the AED remote monitoring device; establish a communications connection between the mobile device and the remote management server; and program the AED with an updated configuration via at least one of the mobile device or the AED remote monitoring device. In embodiments, the updated configuration programming accounts for any prior AED status information communicated to the mobile application during a prior self-test.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIGS. 11A-C are screenshots of the interface of a mobile application for remote monitoring of AEDs shown on a mobile device, according to an embodiment.

Figure 1:
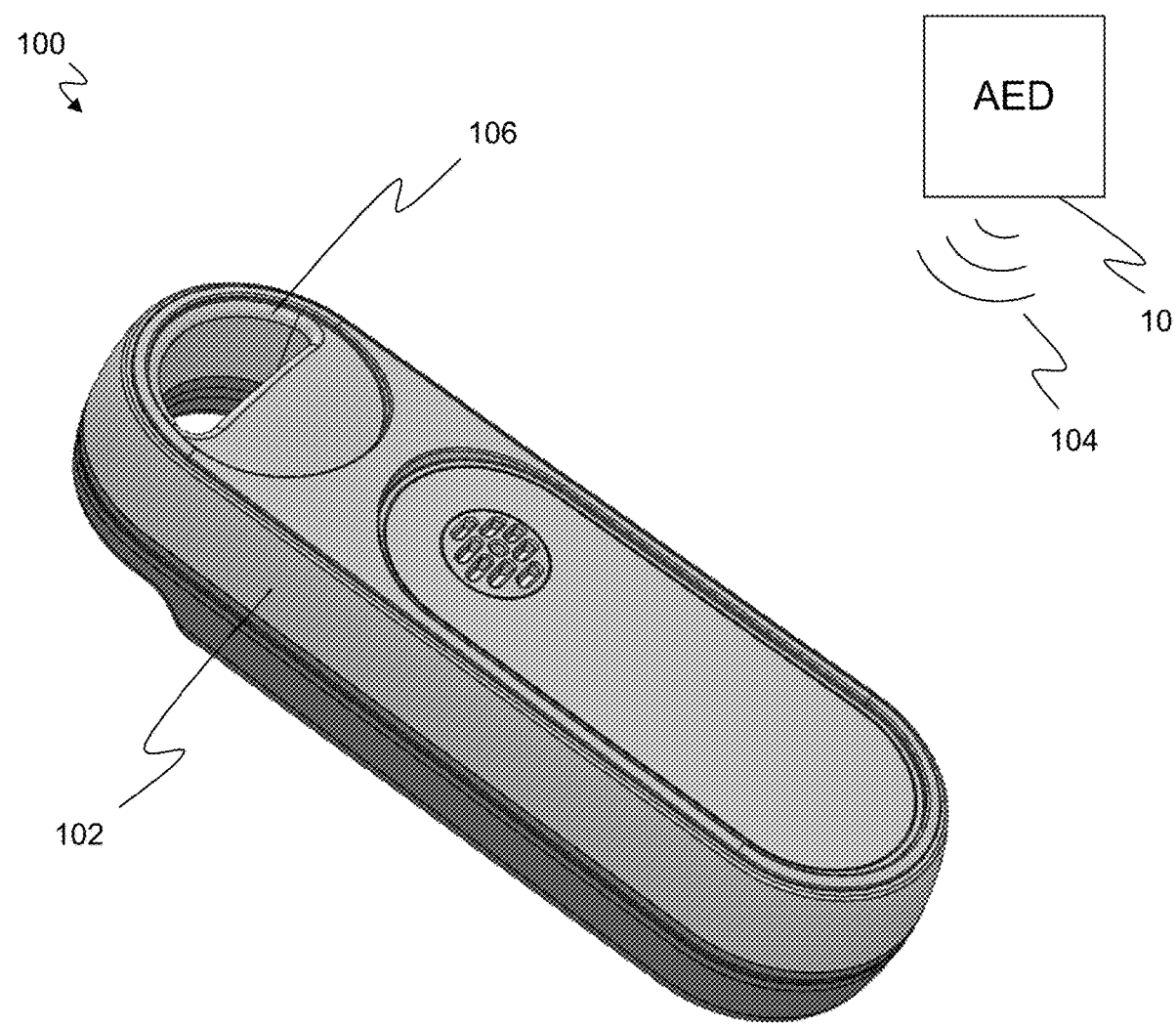
FIG. 1 is a perspective view of a remote monitoring device, according to an embodiment.

While various embodiments are amenable to various modifications and alternative forms, specifics thereof have been shown by way of example in the drawings and will be described in detail. It should be understood, however, that the intention is not to limit the present disclosure to the particular embodiments described. On the contrary, the intention is to cover all modifications, equivalents, and alternatives falling within the spirit and scope of the subject matter as defined by the claims.

DETAILED DESCRIPTION OF THE DRAWINGS

AEDs provide accessible life-saving tools that must be ready for rapid use. In order to maintain this readiness, it is beneficial to employ AED monitoring devices that are either internal or external to an AED. Such AED monitoring devices are configured to detect indications that an AED is in need of maintenance and then send information to a remote location to provide, for example, an indication of a need for service or attention for the AED.

AED monitoring devices according to the present disclosure are advantageously designed to address existing limitations. For example, embodiments described herein reduce power consumption by monitoring devices so that they are not required to expend significant power continually or periodically detecting audio or visual indications from an AED, while also being able to detect noise and nearby sounds/data. AED monitoring devices of the present disclosure also limit power expenditure that is typically required in identifying tones that determine maintenance conditions requiring attention, and hence, limit the frequency of battery replacement. As a result, embodiments of the present disclosure reduce significant maintenance of these monitoring devices themselves which would otherwise undermine efforts to minimize maintenance trips and checking up on devices in person.

Embodiments of the present disclosure address existing problems of battery consumption and poor AED audio tone determination, for example, by using a combination of two separate audio detection circuitries (such as a separate analog microphone and a separate digital microphone, for example) as a listening structure for detecting AED tones. In disclosed arrangements, a first audio detection circuitry can be of low power consumption. The first audio detection circuitry only triggers further evaluation by a second higher power consumption circuitry of greater certainty when certain conditions are met. Accordingly, battery life of a remote monitoring device is extended, frequent power source replacement is unnecessary, and long-term reliability is achieved by embodiments disclosed herein.

For example, a remote monitoring device with minimal battery consumption would be particularly useful in situations where an AED is deployed at a location that may not be specifically visited or maintained for a year or multiple years. Under typical conditions for some embodiments, a remote monitoring device could be expected to have its battery or batteries last for at least four years without requiring replacement. This type of time frame for embodiments of the remote monitoring device can be reliably achieved under proposed embodiments despite reliance on off-the-shelf batteries that are not necessarily well controlled for longevity of power output. The flexibility and long-term reliability that this provides to users maintaining AEDs can be advantageous. Moreover, having a second audio sensor, such as a digital microphone, that is capable of providing a high level of discriminating analysis, and that is also redundant in certain respects of the first audio sensor, provides an advance to achieving monitoring devices of reliable structure.

In some embodiments, listening arrangements can provide various states by the processor of a remote monitoring device which allow for such low power consumption and extended lifetime performance. The states of the device made possible can include a default low power sleep state, a detection state for wakeup confirmation, a listening state for alert confirmation, and a transmission state. Efficient monitoring of power consumption is achieved by such an arrangement involving device states and associated functional operations.

Another issue that is addressed by remote monitoring devices described herein is the problem of false detection of nuisance noises. AEDs can sometimes be located in very noisy environments in public places. For example, AEDs may be located near gymnasiums, workout rooms, or pools in fitness facilities, community centers or schools. Likewise, significant background noise is often found at AED locations in malls, front desks of busy buildings, amusement parks and transportation sites, and construction environments. Furthermore, the ambient and nuisance noise from such environments can vary greatly over the course of a day and from day to day. Accordingly, distinguishing nuisance noise from AED produced audio signals is extremely important as false positive alerts undermine the ability of an audio monitoring device to function properly and can waste important AED maintenance resources to follow up on.

Embodiments disclosed provide arrangements in which successive beeps are detected by a monitoring device with increasing discrimination. This approach prevents nuisance noise from being incorrectly identified as an alert beep from the AED. In some embodiments, an advantageous listening structure arrangement is disclosed in which at least three audio beeps are used to confirm an AED signal and trigger transmission of an alert to a monitoring system. This type of triple check provides extra confirmation that detected signals have the appropriate signatures and occur within the appropriate intervals. This arrangement serves to reduce false positive detection of signals and increases confidence in the reporting conducted by the monitoring device. Multiple confirmations of signals received in order proves to be an effective means at filtering out sounds that are merely nuisance noise and not actually beeps or audio signals from the AED indicative of self-test failures or maintenance requests. An example situation where this triple check could be useful from a user perspective could occur if significant noise resulted in detection of two incorrectly identified chirp sounds in a noisy public environment where audio signals matching a variety of criteria could be inadvertently produced. Without the third check, an unacceptable false positive could occur at times. Unnecessary maintenance and service requests and resource commitments could result. In these embodiments, the third check can largely eliminate this type of false positive detection, as it would be extremely unlikely that mere nuisance noise could match any actual AED alert signal for all three checks.

Other issues that are overcome by embodiments of the present disclosure, for example, may relate to tracking whether the monitoring devices themselves are functioning properly, such as in monitoring for things like battery failure or errors. Unreported failures of monitoring devices can result in AED failures themselves not being reported. Further, unreliable alerts of monitoring device failures only serve to require additional undesired maintenance. Embodiments disclosed include a self-test capability for remote monitoring devices themselves, such that appropriate maintenance of these devices can be carried out when necessary and the integrity of the reporting system is achieved.

An example situation where this feature might be particularly useful could be in instance where an error in the remote monitoring device circuitry occurs or a faulty battery is present in the device. The self-test feature for the remote monitoring device can allow a remote system to determine if the remote monitoring device has detected a communication error with the AED, such as the remote monitoring device not being within a general proximity of the AED, or the remote monitoring device has not checked in with the remote system for a designated period of time such that a no-check in alert can be made. This enables a user to correct the issue with the remote monitoring device quickly and provides confidence in its ongoing integrity over time.

Other issues that monitoring devices in accordance with the present disclosure addresses are the challenges associated with set-up, provision, and appropriately group monitoring devices with the AEDS the monitoring devices are intended to monitor. Embodiments disclosed herein address this issue by providing a mobile app that allows for communication between a mobile device and a remote monitoring device to configure the remote monitoring device. Accordingly, the mobile app is configured to effectively link the remote monitoring device to the AED that it is monitoring. Methods of controlling the mobile app and further disclosure related to these embodiments are included as well.

Examples of situations where this can be particularly useful to users include instances where an AED is being deployed with a remote monitoring device to establish a pairing for the first time the remote monitoring device or the AED is installed. Utilizing the mobile app to associate and link a remote monitoring device to an AED and simultaneously identify a location of this pairing with the GPS of the mobile device running the mobile app saves significant time and reduces user error in set-up. Later updates can efficiently be provided quickly and easily utilizing this known pairing as well.

Embodiments disclosed relate to devices, systems, and methods that enable enhanced remote monitoring and management of one or more AEDs 10, so that proper maintenance and readiness can be provided to these life-saving medical devices.

FIG. 1 shows an example of a remote monitoring device 100 from a perspective view. The remote monitoring device 100 is relatively small in size and largely enclosed in a housing 102 which generally surrounds the internal hardware that is located therein. Numerous other sizes and shapes of housings 102 are possible. At times, throughout the specification and figures, the remote monitoring device 100 may alternatively be referred to as an "AED Tag", "AED monitor", or "AED monitoring device" and should be broadly interpreted and understood to encompass this terminology.

The remote monitoring device 100 is intended for physical co-location with an AED 10. Specifically, the remote monitoring device 100 is intended for location within the general proximity of an AED 10 such that audio sounds 104 made by the AED 10, providing important audio signals that provide information related to the operational status of the AED 10 (e.g., whether the AED and/or parts associated therewith are fully functional), can be detected by the remote monitoring device 100. Accordingly, the remote monitoring device 100 is designed to have the capability to detect the acoustical tones that an AED 10 emits when it requires service or otherwise is providing an update as to its functional status.

In some embodiments, the AED 10 and the remote monitoring device 100 may each be equipped with short-range communication circuitry for short-range PAN communication protocols such as the IOT or BTLE. In embodiments, the effective communication range of such short-range PAN communication protocols is consistent with the general proximity of the AED 10 to the physically co-located remote monitoring device 100 covering a range for effectively monitoring acoustical tones 104 that an AED 10 emits. In some the status of communication channels between the remote monitoring device 100 and either or both the AED 10 and the centralized monitoring server/system can also be monitored and can report an indication to the centralized monitoring server/system that the remote monitoring device 100 is functional and is positioned in close enough proximity to the AED 10 so as to be able to receive a readiness signal, such as from an audible tone and/or from a local NFC or RFID communication.

The housing 102 can include an aperture 106, for example, that can be used for facilitating attachment to the AED 10 and/or be held in close proximity to the AED. This can be done with the aid of a zip-tie, clip, string, hook and loop fastening member or any other coupling structure to the handle or other convenient feature on the AED 10. Attaching the remote monitoring device 100 to an AED 10 or other feature in close proximity to the AED can be done in many different ways and attachment via the aperture 106 should not be deemed to be limiting. In some embodiments, the remote monitoring device 100 may be affixed to the AED such that the remote monitoring device 100 can be stored within a carry case, cabinet or other suitable storage location for an AED 10 and/or other medical equipment. Such a carry case, cabinet or other location can provide a storage location for optimum placement for detection of an AED self-test beep and provide protection to the monitor when deployed in the field with the AED 10. Placement of a remote monitoring device 100 such that it is affixed to an AED 10 near a beep emitting speaker can help ensure optimum performance. In some embodiments, the remote monitoring device 100 may not actually attach to the AED, but instead be stored within a carry case, cabinet or other location for an AED 10 and/or other medical equipment.

In some embodiments, the remote monitoring device 100 may largely be treated as a communication tag for external AED 10 attachment. No particular structure or alignment of attachment location of the remote monitoring device 100 relative to the AED 10 is necessary. Rather, any structure or arrangement within the proximity of the AED 10 such that audio sounds 104 can be detected may be sufficient for the remote monitoring device 100 to be able to report on the functional status of the AED 100. This allows for considerable flexibility with regards to placement and/or attachment of the remote monitoring device 100 and even potential use with a variety of models, types, or brands or AEDs and similar devices, in some embodiments. Likewise, other embodiments of a remote monitoring device 100 may include a monitoring device integrated within an AED carrying case itself, a monitoring device within an AED wall mount (e.g., medical equipment cabinet), a monitoring device within an AED communication station, a monitoring device included as part of an AED accessory (electrode pad, CPR assist device, or resuscitation supplies, etc.), or external security device. In some embodiments it may be thin, small, or otherwise discrete in profile. Other embodiments may be larger in size if necessary.

Figure 2A:
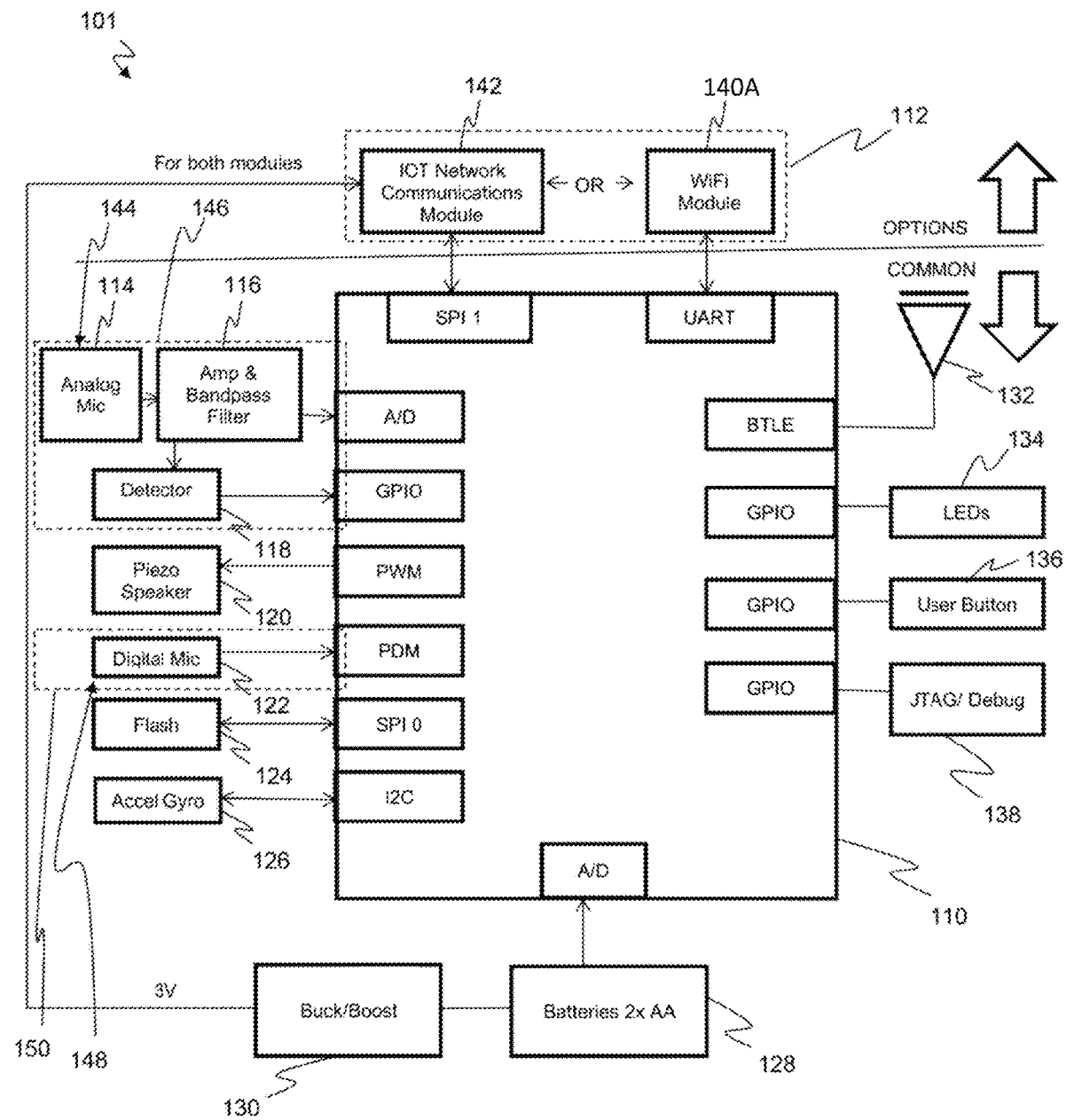
FIGS. 2A-2B each is a hardware architecture diagram of a remote monitoring device, according to an embodiment.
Figure 2B:
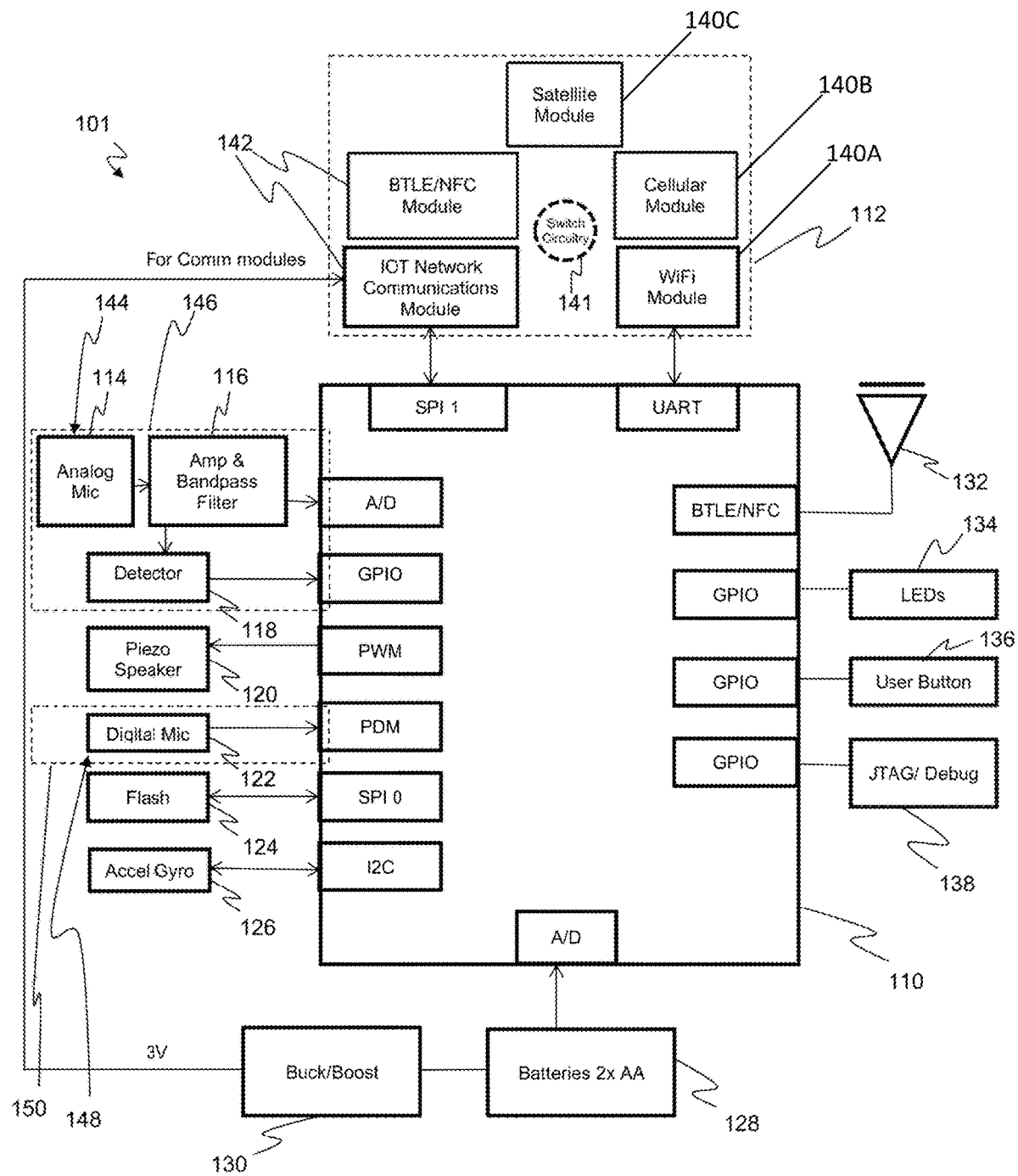

FIGS. 2A and 2B each shows a hardware architecture diagram 101 of one illustrative embodiment of a remote monitoring device 100. The remote monitoring device 100 includes a processor 110 operably coupled with: a communication module 112, a microphone 114, an amplifier and bandpass filter 116, a detector 118, a speaker 120, a microphone 122, a memory 124, and an accelerometer 126. Also shown for powering the processor 110 and communication module 112 are batteries 128 and a boost converter 130. Further, operably coupled with the microprocessor 110 is an antenna 132 for short-range PAN wireless communications protocols such as BTLE or IOT, LEDs 134, a user button 136, and a programming port 138.

Processor 110 can represent at least one processor. In some embodiments, multiple processors or combinations of processing components are contemplated. One example of a processor is a Nordic Radio NRF52832 processor which is an Advanced RISC Machine (ARM)-based System on Chip (SOC) with a Bluetooth radio as a primary on-chip peripheral. Various other processors are contemplated as well.

Communication module 112 may be a wired or wireless communication module. Depicted in FIGS. 2A and 2B are exemplary options of a wireless LAN Internet (Wi-Fi) communication module 140A, a WAN Internet (cellular) communication module 140B, and/or a WAN satellite communication module 140C, and a wireless IOT network communications module 142A and/or BTLE communications module 142B configured for short-range communication protocols. Communication module 112 may serve as the primary wireless connection for the remote monitoring device 100 to the Internet in some embodiments, or from the AED 10 to the Internet via the remote monitoring device 100 in other embodiments. The communications module 112 can send messages to a cloud-based server. A Wi-Fi communication module 140A can wirelessly connect to a router or, alternatively, an IOT network communication module 142 can wirelessly connect to a gateway. Other suitable communication protocols not expressly described above may be employed by the remote monitoring device.

Microphone 114 can be a low power analog microphone in some embodiments. Such an analog microphone 114 can be considered a first audio sensor 144 in some embodiments and work together with a combination of amplifier and bandpass filter 116, a detector (comparator) 118, and other related circuitry that comprise a first audio detection circuitry 146. These components can be used to produce an interrupt to power on or otherwise be activated from a standby mode to the processor 110 when the amplitude of the audio sound signal detected from audio sounds 104 is above a predetermined threshold. The analog signal chain can have its own voltage domain which can be turned on and off to conserve power in some embodiments. In certain embodiments, the first audio sensor 144 could alternatively be a low power digital sensor and first audio detection circuitry 146 could be a digital circuitry as well.

Speaker 120 can be a piezo speaker in various embodiments, although other types of speakers can be used as well. The speaker 120 can generate an audio tone for a self-test of the remote monitoring device 100 itself. The digital speaker 120 can provide high quality digital audio via a Pulse Density Modulation (PDM) interface. The PDM interface can enable input of pulse density modulated signals from the external digital microphone. Input of data is supported by, and data can be transferred to, the processor 110, for example.

Microphone 122 can be a digital microphone. A digital microphone 122 can serve as a second audio sensor 148 in some embodiments. Further, the detection circuitry associated with the digital microphone 122 can be referred to as a second audio detection circuitry 150 in various embodiments. Second audio detection circuitry 150 can include a variety of other types of forms as well.

As discussed above, having a second microphone or audio sensor, such as second audio sensor 148 is generally distinguishing over prior monitoring devices which are known to rely on a single audio sensor. By using two separate audio sensors, this allows the first audio sensor to be one of low power consumption and can be used to as a gatekeeper. Specifically, the first audio sensor restricts use of the second audio sensor, which is more accurate but requires considerably more power, to instances where an initial set of signal criteria are met by audio sounds detected by the first audio sensor. In this arrangement, nuisance noises that are detected and which clearly do not match the criteria of an AED sound or signal can be dismissed without having to expend significant amounts of battery power. The power consumption savings from this arrangement, allows the battery of the remote monitoring device to have sufficient power for years of use without the danger of battery depletion. In various embodiments, a battery life of at least four years can be expected from such an arrangement. The long-term reliability of such an arrangement provides significant advantages over prior monitoring devices.

Memory 124 can include a serial flash memory IC, for example, in some embodiments and can be used to save configuration settings and firmware upgrades such as binary file. Further, the memory 124 can be used to log data.

Accelerometer 126 can optionally be present in various embodiments of the remote monitoring device 100 in order to generate an interrupt signal causing the processor 110 to power on or otherwise be activated from a standby mode in response to detected motion. This can be advantageous as it can provide an indication that the AED 10 is about to be used. In one example, a bystander who witnesses a medical event and decides to obtain an AED would pick-up and move the AED prior to its use. The movement detected by the accelerometer could generate a signal to be sent to the processor(s) which causes the processor(s) to power on. Similarly, in another example, just prior to use, an AED could be removed from a wall case where it resides in an upright location. Reorienting the upright AED to an orientation largely horizontally resting against the ground could be a movement detected by the accelerometer that could generate a signal to be sent to the processor(s) and causes them to power on. This type of monitoring and command to power on or activate from a standby mode can be in addition to the audio sounds monitoring and commands to power on or activate from a standby mode primarily described in this disclosure.

Batteries 128 shown in FIGS. 2A and 2B represent an onboard power source for the remote monitoring device 100. In various embodiments, the remote monitoring device 100 can be powered by two AA cells, although other power sources may be employed (e.g., other types/sizes of batteries, rechargeable batteries, power supply, etc.). The coupled boost converter 130 can be used to generate a stable voltage (e.g., 3.3 volts) for the Wi-Fi communication module 140A and IOT network communications module 142, for example. In alternate embodiments, the remote monitoring device 100 can be line-powered or powered by different battery arrangements.

Antenna 132 is present for PAN short-range communications, such as BTLE for example. BTLE communications are those of a wireless personal area network technology similar to Bluetooth. BTLE communications permit a similar communication range to be used as Bluetooth but provide a significant reduction in power consumption required. Communications using this antenna 132 can be useful in the initial provisioning and setup of the remote monitoring devices 100. In some embodiments, the digital listening state can monitor audible signals from the AED, one-way short-range PAN wireless signals from the AED, or a combination of both, including in various embodiments configured to monitor both signals for confirmation and/or verification of one or both of wakeup signals or status signals to reduce false positive alerts.

LEDs 134 and single user button 136 may generally represent a substantial portion of the user interface for the remote monitoring device 100. One or more LEDs 134 are possible and may be bi-color in various embodiments. Various communication and alerts are made possible with these lights.

Programming port 138 is used for debugging and programming of the remote monitoring device 100. Specifically, the port 138 allows software development and programming of the processor 110.

Figure 3A:
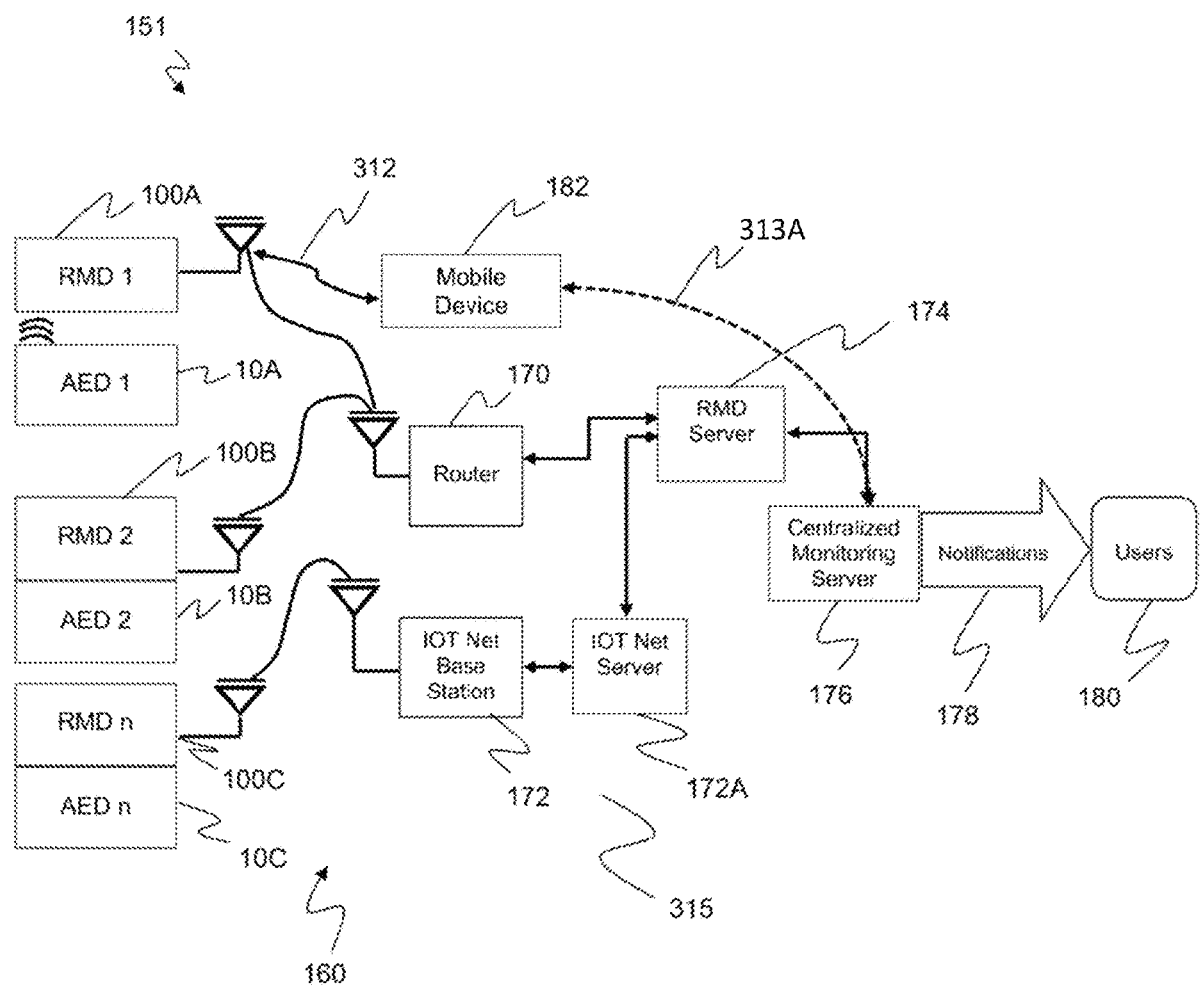
FIGS. 3A-3B each is a diagram of a system for remote monitoring, according to an embodiment.
Figure 3B:
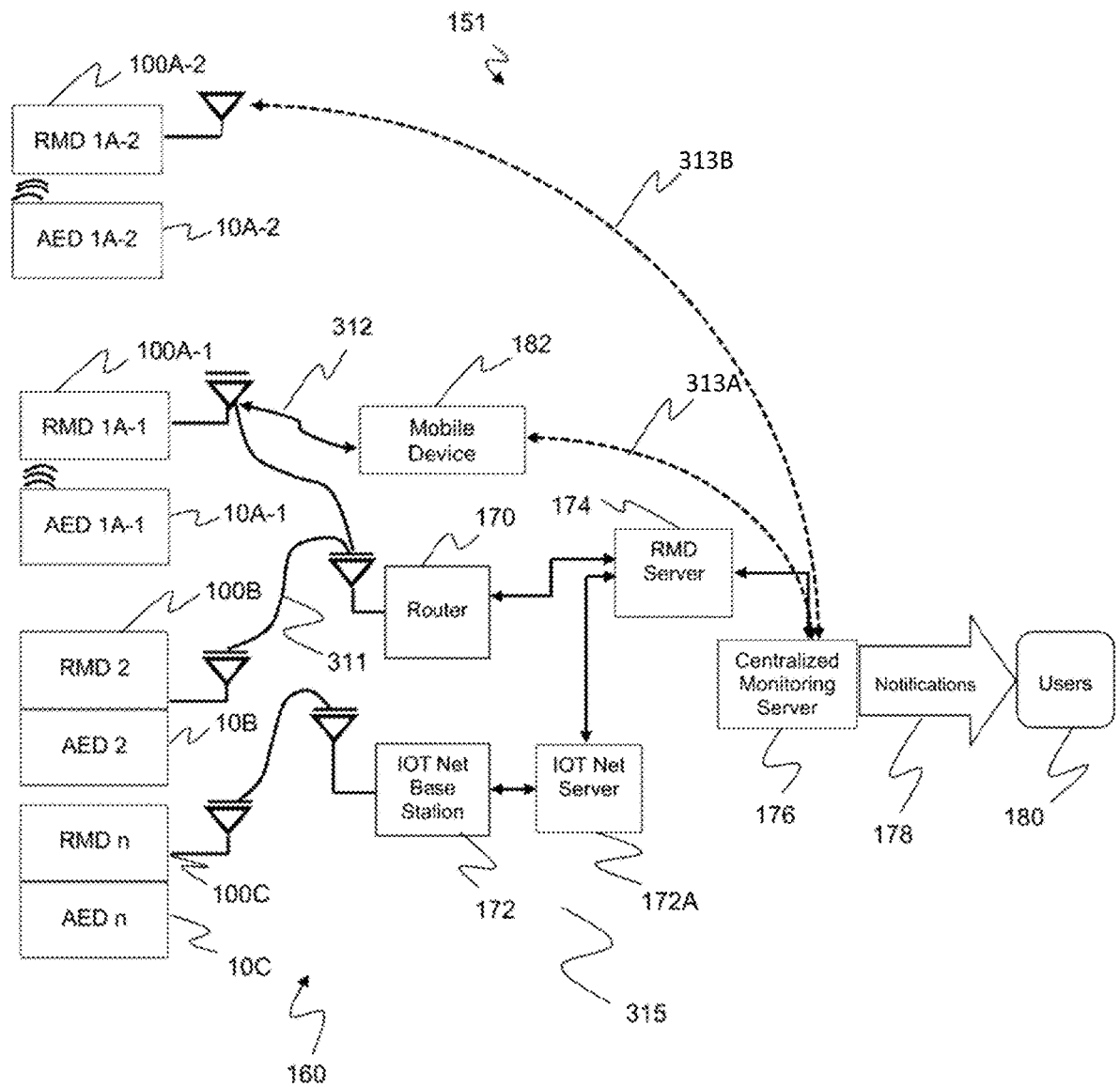

FIGS. 3A and 3B generally depicts an illustrative embodiment of the present disclosure, showing a diagram of a system 151 for remote monitoring and the associated communications network 160. Shown in this figure are a plurality of AEDs 10 (individually shown and referred to at times with reference numerals 10A, 10B, and 10C here) as well as a corresponding, co-located and attached remote monitoring device 100 (individually shown and referred to at times with reference numerals 100A, 100B, and 100C here). Each remote monitoring device 100 has the capability to detect the audio sounds 104 in the form of acoustical tones that an AED 10 emits when it requires service.

The remote monitoring devices 100 also have the capability to wirelessly connect to a router 170 (for Wi-Fi based remote monitoring devices 100A and 100B, for example) or a gateway 172 and associated server 172A (for IOT network based remote monitoring devices 100C, for example) to send messages to a cloud-based remote monitoring device server 174 (such as on Amazon® Web Services (AWS), for example). The remote monitoring device server 174 handles the transactions with each remote monitoring device 100, maintains a remote monitoring device database, and exchanges messages between a centralized monitoring service or server 176 and the AED remote monitors 100. Monitoring service or server 176 provides a proprietary back end that coordinates AED kit data. Monitoring service or server 176 maintains the status of the AEDs 10 and can push notifications 178 to the appropriate stakeholders or users 180 as necessary.

In some embodiments, the server 176 can be embodied by a centralized monitoring server and monitoring service, for example. Other servers, services and systems and tools are possible as well. The embodiment related to the particular centralized monitoring server described herein is not limiting. Existing centralized monitoring servers and monitoring services have been developed for managing various AED services. These services can provide functionality like scheduling, ordering of supplies, and even payroll information functions for educators, and email/text/phone messaging to AED owners in the field. This is facilitated by the software and applications providing a user interface to AED owners. External inputs, such as remote monitoring device messages via Wi-Fi, can be routed to the server 174, then routed to the server 176 for storage and response management. At times, server 176 will also be referred to as a monitoring service, centralized monitoring service, centralized monitoring server, or remote management server.

Further, seen in FIGS. 3A and 3B is a mobile device 182. Mobile device 182 can be a phone, tablet, or other range of appropriate electronic devices. Mobile device 182 provides a separate communication link to the remote monitoring devices 100 that can be utilized in the provisioning process for the remote monitoring devices 100 and corresponding AEDs 10, and will be described later in greater detail.

Figure 4:
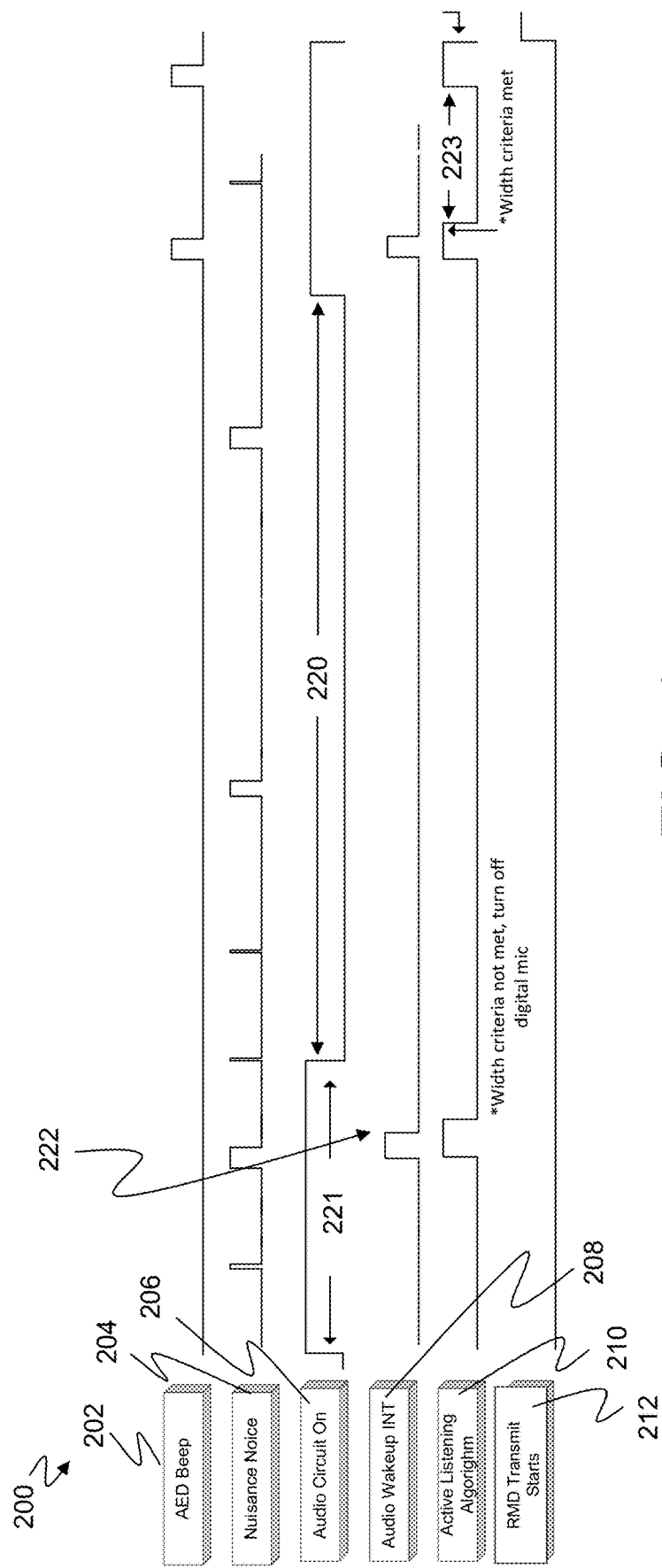
FIG. 4 is a diagram of an audio circuit and active listening timing diagram, according to an embodiment.

As understood from an example scenario shown in FIG. 4, the structure for the listening algorithm utilized by the remote monitoring device 100 helps determine how the device and its related systems function. To illustrate this, FIG. 4 shows a diagram 200 of an audio circuit and active listening timing, according to an embodiment. Lines indicative of events are shown adjacent one another on the timing diagram and include representations of: AED beeps at 202; nuisance noises at 204; a first audio detection circuitry 146 powered on at 206, an audio wakeup interrupt at 208; an active listening algorithm 210; and an indication of when a transmission of the remote monitoring device 100 starts at 212.

In the example embodiment illustrated, a first audio detection circuitry 146 can be analog and operably connected to a first analog audio sensor 144 and processor 110. Further, a second audio circuitry 150 can be digital and operably connected to a second audio sensor 148 that is digital.

Note that in alternate embodiments, other audio sensor configurations could be possible as well. For example, the audio sensors may not necessarily need to be a combination of analog and digital microphone. The remote monitoring device 100 could instead rely on two digital microphones, three microphones, or other combination of audio sensors.

Initially, the remote monitoring device 100 will duty-cycle power to the first audio detection circuitry 146 according to a listening interval configuration setting providing a predetermined detection interval 220 to conserve power (such as between 2-240 minutes, 5-120 minutes, 10-60 minutes, 30 minutes). Other configurable listening intervals are contemplated as well. In some embodiments, the detection interval period is a constant such that, once set, there is no need to have the detection interval updated or compared to a clock value which can eliminate the power needs for a separate clock circuit component. As seen at line 206 in FIG. 4, the remote monitoring device 100 can turn on the first audio detection circuitry 146 for a listening interval 221. The listening interval may be configurable and set according to a particular amount of time (such as between 10-120 seconds, 20-60 seconds, 30-50 seconds, 35 seconds, etc.). In various embodiments, the listening interval is generally less time than the detection interval (such as on the order of seconds for the listening interval versus minutes for the detection interval). In various embodiments, the detection intervals and/or the listening intervals may be set so that the periods are long enough to catch initial and subsequent beeps or qualifying audio tones, but not so long as to drain battery energy unnecessarily. In various embodiments, the relationship between a period of the detection interval and a period of the listening interval is generally corresponding such that a longer listening interval is used for a longer detection interval and a shorter listening interval is used for a shorter listening interval.

The first audio detection circuitry 146 generates a wakeup notification signal 222 when it detects audio sounds during the predetermined detection interval 220. This is shown at 208 in FIG. 4. The second audio sensor 148 is powered on in response to the wakeup notification signal 222 and commences an active listening mode with an audio listening algorithm 210 to provide digital audio signals to the processor 110. If the algorithm 210 does not qualify the audio as an AED beep/tone, the digital microphone 122 will be powered off. If a qualified beep/tone is detected, the digital microphone 122 will be muted for a time interval 223 which may be, for example, dependent on the AED Model (for example, this could be a precise time between 25 and 35 seconds for a Cardiac Science® G3 AED and a different precise time between 25 and 35 seconds for a Cardiac Science® G5 AED), and will remain on for up to an additional interval of precise time period to attempt to detect and qualify a second beep. In some embodiments, this additional interval can be a time period (such as between 4.0-6.0 seconds, 4.0-5.0 seconds, 4.6-5.0 seconds, 4.8 seconds, etc.). If a qualifying second beep/tone is detected, the digital microphone 122 will remain on up to another listening interval to look for a third qualifying tone. In some embodiments, this listening interval may be configurable and set according to a particular amount of time (such as between 10-120 seconds, 20-60 seconds, 30-50 seconds, 35 seconds, etc.).

In general, the processor 110 is configured to power on in response to the wakeup notification signal 222, process the digital audio signals, and transmit a signal to the monitoring service 176 to report a condition of the AED 10 based on the digital audio signals that are processed. In other embodiments, the digital listening state can also monitor one-way short-range PAN wireless signals from the AED, or a combination of both PAN wireless and digital audio signals, including in various embodiments configured to monitor both signals for confirmation and/or verification of one or both of wakeup signals or status signals to reduce false positive alerts.

Described another way, the second audio circuitry 150 can be understood to include an audio listening algorithm 210 that is initiated when an audio wakeup interrupt 208 occurs. In some embodiments, the second audio sensor 122 (digital microphone) can stream 16 kHz PDM data into 128 sample buffers which are processed by the audio listening algorithm 210. This processing can include the output of a decimator being compared to an adaptive threshold, and pulse timing characteristics being computed based on the time the signal is above the threshold. In an embodiment as described more fully below in connection with the description of FIG. 5, the audio listening algorithm 210 identifies the presence of three consecutive qualifying pulses. Pulses are qualified based on criteria or qualification parameters such as pulse width and pulse interval. Other pulse qualification parameters could be utilized as well such as frequency, amplitude, intensity, or other waveform features.

In various embodiments, the number of qualified pulses can be configured to be three or more pulses that meet the same pulse qualification parameters, and in other embodiments, the number of qualified pulses can be configured to be a consecutive sequence of one or more pulses that meet a different set of qualification parameters for different positioned pulses in a sequence of at least two pulses or of at least three pulses. The qualification criteria or qualification parameters of the pulses may be different for different models of AED 10 and may be set based on a model type communicated to the remote monitoring device 100 from the centralized monitoring service or server 176 during provisioning or initialization. Accordingly, in some embodiments, a device is contemplated having a listening structure where a first audio detection circuitry 146 powers on, or otherwise activates from a standby mode, a second audio detection circuitry 150 to trigger a transmission report and determine that an audio beep detected is qualifying Specifically, a remote monitoring device 100 can monitor and manage by a monitoring service (such as centralized monitoring service or server 176 with a database via a communications network 160, for example) a condition of an AED 10 (such as whether service is required) based on audio signals from the AED 10. The remote monitoring device 100 includes a housing 102 that is configured to be positioned outside of the AED 10 such that audio sounds 104 from the AED 10 can be detected. The housing 102 contains at least one processor 110, a communications module 112, a first audio sensor 144, a first audio detection circuitry 146, a second audio sensor 148, and a second audio detection circuitry 150. In some embodiments, the first audio sensor 144 includes an analog microphone 114 that detects audio sounds 104 based on an initial audio threshold of at least one of sound amplitude and/or sound frequency.

In some embodiments, the first audio sensor 144 can be dynamically modified to respond to changes in the environment of the AED 10. For example, in very loud environments that continue to cause the remote monitoring device 100 to power on the second audio detection circuitry 150 in response to a wake up notification signal 222, but the second audio detection circuitry 150 determine that the noises triggering the wake up notification signal are only "nuisance events," the processor 110 can adjust one or both of the time periods for the detection interval and/or listening interval in an effort to avoid or reduce such nuisance events to help conserve power. In some embodiments, the processor 110 may evaluate a set of detection intervals to selectively adjust detections intervals in an effort to avoid or reduce detection during the day and increase detection during the night. In other embodiments, the processor 110 may be provided with an ability to dynamically adjust the initial audio threshold of the analog microphone 114 by, for example, writing to a port that adjusts a parameter of the microphone, an effective equivalent of an input circuit, or a power to an amplifier associated with the microphone.

Additionally, the communications module 112 is operably connected to the at least one processor 110 and configured to transmit electronic communications to the monitoring service 176 via the communications network. In some embodiments, the communications module 112 is configured to wirelessly transmit electronic communications. This can be done via one of Wi-Fi or IOT network, for example.

Additionally, the first audio detection circuitry 146 can be operably connected to the first audio sensor 144 and the at least one processor 110. The first audio detection circuitry 146 is configured to power on during a predetermined detection interval 220 and generate a wakeup notification signal 222 when the first audio detection circuitry 146 detects qualifying audio sounds 104 during the predetermined detection interval 220. In some embodiments, the first audio detection circuitry 146 is analog.

The first audio detection circuitry 144 is continuously powered separate from processor 110 and is of significantly lower power than required by processor 110. In general, processor 110 runs based on a first detection of audio, then qualifies based on more detailed analysis of the signal.

In an alternate embodiment of the design, a digital audio buffer could be added to the digital microphone so that when processor 110 turns on based on analog detection, it can query the digital microphone buffer for pulses already recorded. This eliminates the need to stay on to wait for a qualifying pulse. The previous pulse already recorded and stored in digital mic buffer running could then be used without having to turn the processor 110 on.

The second audio detection circuitry 150 is operably connected to the second audio sensor 148 and the at least one processor 110. The second audio detection circuitry 150 is configured to power on in response to the wakeup notification signal 222 and commence an active listening mode to provide digital audio signals to the at least one processor 110. In some embodiments, the second audio detection circuitry 150 is digital.

In some embodiments, the second audio detection circuitry 150 is able to be powered on in less than ten milliseconds from a detection of qualifying audio sounds 104 by the first audio sensor 144 that satisfy an initial audio criteria. In some embodiments, the second audio detection circuitry 150 is configured to be powered on in less than one millisecond from detection of audio sounds 104. In some embodiments, the second audio detection circuitry 150 is configured to be powered on between 0.5 milliseconds and 5 milliseconds from detection of audio sounds 104. In some embodiments, the second audio detection circuitry 150 is configured to be powered on between 1 millisecond and 10 milliseconds from detection of audio sounds 104. In some embodiments, the second audio detection circuitry 150 is turned on prior to completion of an audio sound 104 from the AED 10 initially detected by the first audio sensor 144, shortly or immediately after, or during a subsequent audio sound 104 from the AED 10. The at least one processor 110 is configured to power on the second digital microphone in response to the wakeup notification signal 222, process the digital audio signals, and transmit a signal to the monitoring service 176 to report a condition of the AED 10 based on the digital audio signals that are processed.

In some embodiments, the signal transmitted to the monitoring service 176 identifies a serial number of the AED 10. In some embodiments, the audio sounds 104 from the AED 10 communicate as part of the message, at least one of the following: a self-test failure of the AED 10; a battery expiration; and an electrode expiration. Self-test failures can include failures of internal electronics, buttons, a CPR feedback device, a high voltage circuit (including standard, partial or full energy charge cycle tests of this), and other battery and/or electrode tests, for example.

In some embodiments, the audio sounds 104 from the AED 10 include information based on an encoding scheme, and the processor(s) 110 is configured to analyze the digital audio signals to cause the signal transmitted to the monitoring service 176 to include status information of the AED 10 based on the encoding scheme. In some embodiments, the AED could embed additional information in the audible tone by using different pulse widths and/or intervals to convey specific types of errors, rather than just a generic error has occurred. This encoding scheme could include a frequency shift keying (FSK) technique, for example. This would provide additional information of the error (code), as well as improved Signal to Noise Ratio (SNR). The enhanced SNR could then provide for greater rejection of unqualified audible events using the specificity provided with embedded data codes (vs. just using amplitude, etc.). Other encoding schemes could include encoding that varies inter-beep or inter-pulse timing and length to help determine the type of failure (i.e. self-test, battery expiration, electrode expiration, etc.). Similarly, encoding could be done with a quasi-morse code option in which various beep codes are conveyed. In some embodiments, encoding may be non-audible. Beeps could be designed to have good selectivity and ability to reject noise. In some embodiments, the amplitude of signals could be fine-tuned to provide information about certain high priority alarms. An alarm indicating an AED is unable to perform a rescue could increase amplitude and allow people to hear the alarm clearly. In some embodiments, cadence and volume of beep could be used to encode a level of concern and urgency into the signals.

In some embodiments, the at least one processor 110 is further configured to power down once the signal is transmitted to the monitoring service 176. Likewise, in various embodiments, the processor 110 can be configured to power down if any of a variety of conditions is not met. Conditions could include that a first qualifying tone is not detected in the digital audio signals during a first active listening interval; a second qualifying tone is not detected in the digital audio signals during a second active listening interval; or a third qualifying tone is not detected in the digital audio signals during a third active listening interval.

As discussed above, in some embodiments, power consumption necessary for operation of the first audio detection circuitry 146 is less than power consumption necessary for operation of the second audio detection circuitry 150. Accordingly, relying on low power consumption for basic initial detection and operation of the remote monitoring device 100, enables extended battery life and a device that does not require frequent power source replacement. The advantages to such extended battery life can be significant as the long-term reliability of the remote monitoring device 100 is largely only limited by battery drain over time.

Accordingly, in some embodiments, a device is contemplated having a processor 110 actively control the remote monitoring device components. In some such embodiments, a first audio detection circuitry 146 signals a second audio detection circuitry 150 to wake up and confirm appropriate sound detection and trigger a transmission report. Specifically, a remote monitoring device 100 for monitoring audio signals from an AED 10 and electronically reporting to a monitoring service 176 via a communications network 160 is contemplated. The remote monitoring device 100 includes a housing 102 configured to be positioned outside of the AED 10 such that audio sounds 104 from the AED 10 can be detected. The housing 102 contains a communications module 112, a first audio sensor 144, a first audio detection circuitry 146, a second audio sensor 148, a second audio detection circuitry 150, and at least one processor 110.

Additionally, the communications module 112 is configured to transmit electronic communications to the monitoring service 176 via the communications network 160. The first audio detection circuitry 146 is operably coupled with the first audio sensor 144. The first audio detection circuitry 146 is configured to detect audio sounds 104 from the AED 10 via the first audio sensor 144. The second audio detection circuitry 150 is operably coupled with the second audio sensor 148. The second audio detection circuitry 150 can be configured to detect the audio sounds 104 from the AED 10 via the second audio sensor 148. The at least one processor 110 is operably coupled with the communications module 112, the first audio detection circuitry 146, and the second audio detection circuitry 150.

Accordingly, in some embodiments, a device is contemplated having a listening structure where audio detection circuitry listens for a first signal (to wake up), a second signal (to confirm the signal from the AED 10), and third signal (to confirm the signal from AED 10 again, and trigger a transmission). Specifically, a remote monitoring device 100 is contemplated for monitoring audio signals from an AED 100 and electronically reporting to a monitoring service 176 via a communications network 160. The remote monitoring device 100 includes a housing 102 configured to be positioned outside of the AED such that audio signals from the AED 10 can be detected. The housing 102 contains a communications module 112, at least one audio sensor (i.e. 144 and/or 148), at least one audio detection circuitry (i.e. 146 and/or 150), and at least one processor 110. The communications module 112 is configured to transmit electronic communications to the monitoring service 176 via the communications network 160.

The at least one audio detection circuitry (i.e. 146 and/or 150) is operably coupled with the at least one audio sensor (i.e. 144 and/or 148). The at least one audio detection circuitry (i.e. 146 and/or 150) is configured to detect audio sounds 104 from the AED 10 via the at least one audio sensor (i.e. 144 and/or 148). The at least one processor 110 is operably coupled with the communications module 112 and the at least one audio detection circuitry 146. Further, the at least one processor 110 is configured to: process signals from the at least one audio detection circuitry 146 based on the detected audio sounds 104; detect a first audio signal from the processed signals; in response to the first audio signal being detected, commence an active listening mode to detect a second audio signal from the processed signals and confirm that the second audio signal meets a predetermined criterion associated with the active listening mode; in response to the second audio signal being detected, re-commence the active listening mode to detect a third audio signal from the processed signals and confirm that the third audio signal meets the predetermined criterion associated with the active listening mode, and transmit a report signal to the monitoring service 176 if the third audio signal meets the predetermined criterion.

In some embodiments, the predetermined criterion associated with the active listening mode is different than at least one criteria used by the at least one audio detection circuitry (i.e. 146 and/or 150) to detect qualifying audio sounds 104 from the AED 10. In some embodiments, the predetermined criterion associated with the active listening mode are based on at least one of: a pulse width, a frequency, an amplitude, and a pulse interval, of each tone in the audio signals. In some embodiments, the at least one audio sensor (i.e. 144 and/or 148) mutes for an interval during the active listening mode between the second audio signal and the third audio signal. In various embodiments, the at least one processor 110 is configured to power down if the second audio signal does not meet the predetermined criterion or if the third audio signal does not meet the predetermined criterion.

In addition to the capability to detect the audio sounds 104 in the form of acoustical tones that an AED 10 provides, in some embodiments, the remote monitoring device 100 further includes an optical sensor (not shown) operably connected to the at least one processor 110 to detect whether the AED 10 presents a visual indication of an AED self-test failure. For example, the optical sensor can detect whether a light on the AED 10 is illuminated to indicate an AED self-test failure.

In some embodiments, increases in an amplitude of the audio sounds 104 from the AED 10 are used to convey a level of urgency to be included in the signal transmitted to the monitoring service 176. In some embodiments, an audio sound 104 from the AED 10 is outside an audible range of human hearing. In some embodiments, an audio sound 104 from the AED 10 includes variations in at least one of: an inter-tone timing, and a length, of the audio sounds 104 that are used to convey information to be decoded by the processor(s) 110. In other embodiments, different sets of one-way short-range PAN wireless signals from the AED 10 may be used to convey information to be decoded by the processor(s) 110.

Figure 5:
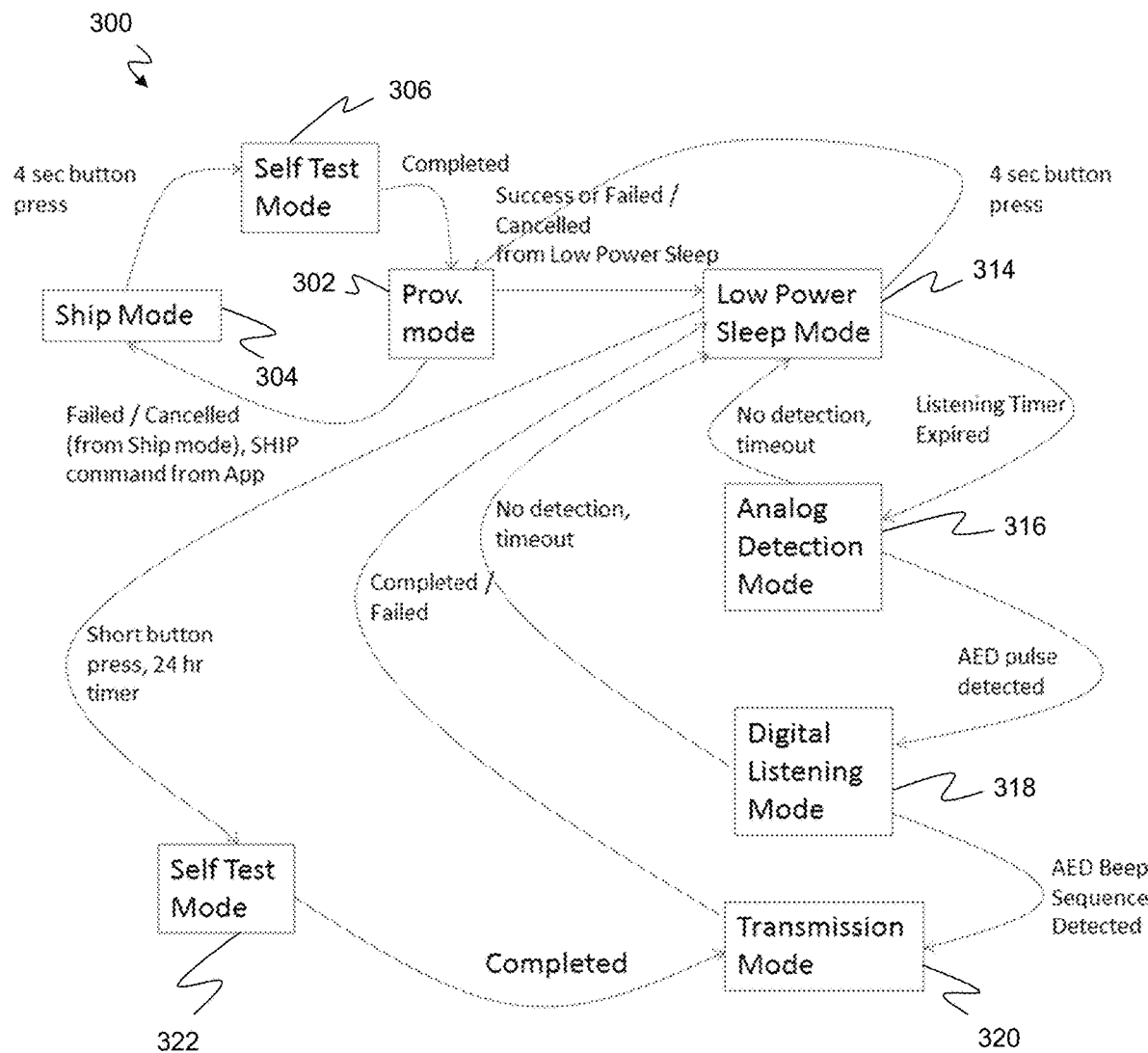
FIG. 5 is a flow diagram of operations for the remote monitoring device, according to an embodiment.

FIG. 5 sets forth a flow diagram 300 of operations for the remote monitoring device 100 and some of its various functional modes. These modes are generally areas of functional responsibility and relate to areas covered in the FIGS. discussed this far. This includes monitoring audio sounds 104 (via audio sensor(s) 144 and 148 and audio detection circuitries 146 and 150), monitoring AED motion (via an accelerometer 126), performing a self-test, and communicating results to a monitoring service 176 through a remote monitoring device server 174. Accordingly, FIG. 5 provides a high-level overview of the modes/states of the remote monitoring device 100 and related methods and systems in performance of operations.

When initially deployed with an AED 10, the remote monitoring device 100 undergoes provisioning and related operations. This is represented in FIG. 5 by provisioning mode 302, ship mode 304, and self-test mode 306 boxes on the diagram 300. In terms of provisioning, it should be first understood that to set up the system, a mobile application 310 running on a mobile device 182 connects to the remote monitoring device 100 via a Bluetooth link 132. (See FIGS. 3A-3B). The mobile device 182 also connects to the centralized monitoring service 176 via a Wi-Fi data link 311 or cellular data link 313A or IOT network link 315. (See FIGS. 3A-3B). In embodiments, the remote monitoring device 100 may also be provided with WAN cellular communication module 142 to enable connection via a cellular data link 313B to the centralized monitoring server 176. A user will use the mobile application to select an AED kit on the centralized monitoring service 176 and associate (i.e. pair) it to the proximate remote monitoring device 100 and enter the location of these as an AED kit. The mobile application 310 is also used to configure Wi-Fi based remote monitoring devices 100 with site-specific parameters, such as network IDs and security credentials using the Bluetooth link 312. In embodiments, the remote monitoring device 100 with connection to the centralized monitoring server 176 via an IOT network connection (172, 172A) using the Bluetooth link 312 or similar short-range PAN network communication protocols such as NFC. In any of the communication channels modes, the remote monitoring device may report AED status, site-specific parameters and/or communication channel status.

Another aspect of the provisioning process involves the self-test mode 306. Following set-up, the remote monitoring device 100 attempts to connect to the centralized monitoring service 176 to download the common configuration parameters. The mobile application 310 and/or remote monitoring device 100 will indicate the success or failure of the connection. The self-test mode 306, provisioning mode 302 and related modes and operations will be described later in greater detail in associated with subsequent figures.

Once provisioned, the remote monitoring device 100 may reside in a low power sleep mode 314. Very little power is expended while in this mode. Upon expiration of a listening timer based on a predetermined detection interval 220, the device transitions to an analog detection mode 316. If no audio sounds 104 are detected to generate a wakeup signal, the device 100 returns to the low power sleep mode 314. If, however, an audio sound 104 is detected during the predetermined detection interval 220 of the analog detection mode 316, the device 100 will transition to a digital listening mode 318 (also referred to at times as active listening mode). If there is no detection of qualifying audio sounds 104 based on processed digital audio signals, the device 100 returns to the low power sleep mode 314. If, however the digital audio signals processed indicate a condition of the AED 10 that requires transmission, the remote monitoring device 100 enters a transmission mode 320. In the transmission mode 320, a signal is transmitted to the centralized monitoring service 176 to report the AED condition. Once this transmission is completed or fails, the remote monitoring device 100 returns to the low power sleep mode 314. Also referenced in FIG. 5, is a self-test mode 322 that can be utilized in response to a short button press or a 24-hour timer. Successful self-test modes 322 will result in notification via transmission mode 320.

Accordingly, in some embodiments, a device is contemplated having a listening structure where a processor has a low power sleep state (including low power sleep mode 314), a detection state (including analog detection mode 316), a listening state (including digital listening mode 318), and a transmission state (including transmission mode 320). Specifically, a remote monitoring device 100 for monitoring audio signals from an AED 10 and electronically reporting to a monitoring service (such as centralized monitoring service 176 via a communications network, for example) is contemplated. The remote monitoring device 100 includes a housing 102 configured to be positioned outside of the AED 10 such that audio signals from the AED 10 can be detected. In various embodiments, the housing 102 contains at least one processor 110, a communications module 112, a first audio sensor 144, a first audio detection circuitry 146, a second audio sensor 148, and a second audio detection circuitry 150.

Additionally, the communications module 112 is operably connected to the at least one processor 110 and is configured to transmit electronic communications to the monitoring service 176 via the communications network 160. In various embodiments, the first audio detection circuitry 146 is operably connected to the first audio sensor 144 and the at least one processor 110, and the second audio detection circuitry 150 is operably connected to the second audio sensor 148 and the at least one processor 110.

The at least one processor 110 is configured to: reside in a low power sleep state (or low power sleep mode 314) by default; commence a detection state (i.e. analog detection mode 316) for wakeup confirmation during a detection interval 220 in which the first audio detection circuitry 146 is configured to power on and generate a wakeup notification signal 222 when the first audio detection circuitry 146 detects audio sounds 104 during the detection interval 220 via the first audio sensor 144; commence a listening state (i.e. digital listening mode 318) for alert confirmation in response to the wakeup notification signal 222 in which the second audio detection circuitry 150 is configured to power on and provide digital audio signals to the at least one processor 110 in an active listening mode (i.e. digital listening mode 318); and commence a transmission state (i.e. transmission mode 320), upon confirmation of at least three consecutive qualifying tones in the audio signals detected in corresponding qualifying intervals during the digital listening state (i.e. digital listening mode 318), in which the communications module 112 is caused to transmit a message to the monitoring service 176 via the communications network 160 indicating a status of the AED 10.

In some embodiments, the transmission state (i.e. transmission mode 320) further includes powering down the second audio detection circuitry 150 once the communication module 112 is caused to transmit a message to the monitoring service 176.

Figure 6:
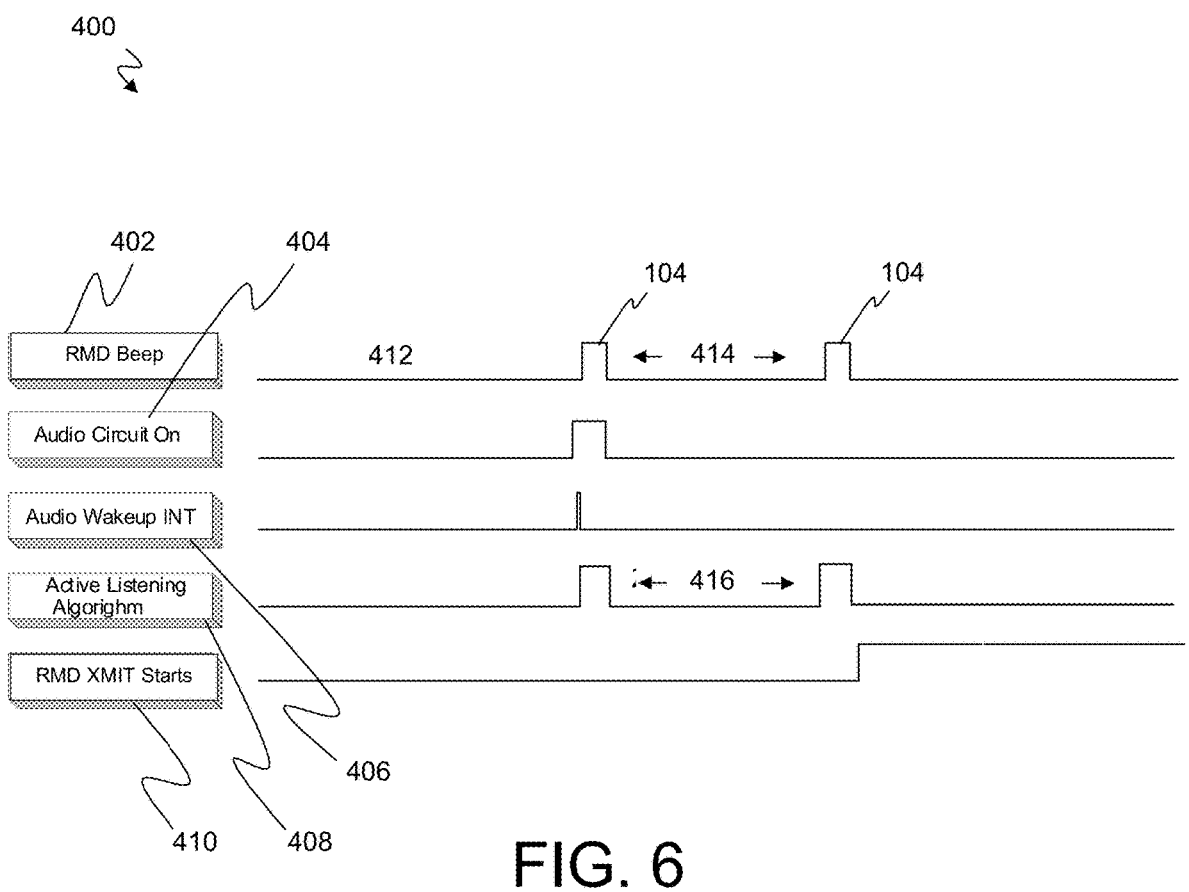
FIG. 6 is a self-test operation diagram for the remote monitoring device, according to an embodiment.

FIG. 6 shows a self-test operation diagram 400 for the remote monitoring device 100 itself. This self-test of the remote monitoring device 100 is independent of any self-tests run by the AEDs 10 that are being monitored. Lines indicative of events are shown on a common chart and include representations of: audio sounds 104 such as beeps of the remote monitoring device 100 at 402; the audio circuit of the first audio detection circuitry 146 at 404; an audio wakeup interrupt at 406; an active listening algorithm of a second audio detection circuitry 150 shown at 408; and an indication of when a transmission of the remote monitoring device 100 occurs at 410.

In the embodiment depicted, the self-test is initiated at 412 via a 24-hour timer started at the time the remote monitoring device 100 is initially provisioned, or by a button press by a user at a later time. The self-test first tests the first audio detection circuitry 146 (i.e. analog audio circuit) by generating a speaker 120 (piezo beeper) tone 104 and confirming an audio wakeup interrupt at 406 occurs. The self-test then tests the second audio detection circuitry 150 (i.e. the digital active listening circuit) by generating a speaker 120 (piezo beeper) tone 104 and confirming the pulse amplitude and duration are sufficient for detection. In some embodiments, a beeper/audio sound 104 is sufficient if within a determined frequency (i.e., between 3-5 KHz, 3.5-4.5 KHz, or 4 KHz) and/or a determined pulse width (i.e. between 200-400 ms, 250-350 ms, or 300 ms), for example. As shown, an interval 414 is present between tones 104. This interval 414 may be between 2-4 seconds, 2.5-3.5 seconds, or 3 seconds, for example. Also depicted, a mute interval 416 for the active listening algorithm is present. This mute interval 416 may be between 2-4 seconds, 2.5-3.5 seconds, or 3 seconds, for example.

The self-test of the remote monitoring device 100 also measures the battery voltages under load of radio transmission. The battery 128 is tested during every transmission and self-test looks at the battery status from the previous transmission. A low battery status is defined as a voltage under 2.2 V. The results of the self-test are stored in memory 124 and a result code for the self-test is transmitted to the centralized monitoring service 176.

Accordingly, various embodiments contemplate a device having a self-test feature. Specifically, a remote monitoring device 100 is disclosed for monitoring audio signals from an AED 10 and electronically reporting to a monitoring service (such as centralized monitoring service 176 via a communications network 160, for example). The remote monitoring device 100 includes a housing 102 configured to be positioned outside of the AED 10 such that audio signals from the AED 10 can be detected. The housing 102 contains at least one processor 110, a memory 124, a communications module 112, a speaker 120 (such as a piezo speaker in some embodiments), at least one audio sensor 144, and at least one audio detection circuitry (i.e. 146 and/or 150). The memory 124 is operably connected to the at least one processor 110.

The communications module 112 is operably connected to the at least one processor 110 and configured to transmit electronic communications to the monitoring service 176 via the communications network 160. The speaker 120 is operably connected to the at least one processor 110 and configured to generate audio sounds 104 as part of a self-test of the remote monitoring device 100. The at least one audio detection circuitry (i.e. 146 and/or 150) is operably coupled with the at least one audio sensor 144.

Additionally, the at least one audio detection circuitry (i.e. 146 and/or 150) is configured to detect audio sounds 104 via the at least one audio sensor 144 and provide digital audio signals to the at least one processor 110. The at least one processor 110 is configured to: periodically cause the speaker 120 to generate the audio sounds as part of the self-test of the remote monitoring device 100; receive the digital audio signals to confirm that the audio sounds 104, as part of the self-test of the remote monitoring device 100, originate from the speaker 120; and transmit a message conveying results of the self-test of the remote monitoring device 100 to the monitoring service 176 via the communications network 160.

In some embodiments, the at least one audio detection circuitry (i.e. 146 and/or 150) is configured to power on during an analog detection interval 220 and generate a wakeup notification signal 222 when audio sounds 104 are detected during the analog detection interval 220. In some embodiments, the at least one audio detection circuitry 146 is configured to power on in response to the wakeup notification signal 222 and commence an active listening mode.

In some embodiments, the housing 102 includes a battery 128 of indeterminate life operably connected to the processor(s) 110 and the communications module 112. In some embodiments, the self-test is further configured to measure a battery voltage of the battery 128 under load during at least two successive transmissions by the communications module 112 to determine if a low battery status is present. In some embodiments, the processor(s) 110 can cause the communications module 112 to provide information related to battery status from the previous transmission. In some embodiments, the self-test is configured to be conducted daily in response to one of a 24-hour timer or physical press of button 136 of the remote monitoring device 100.

Figure 7:
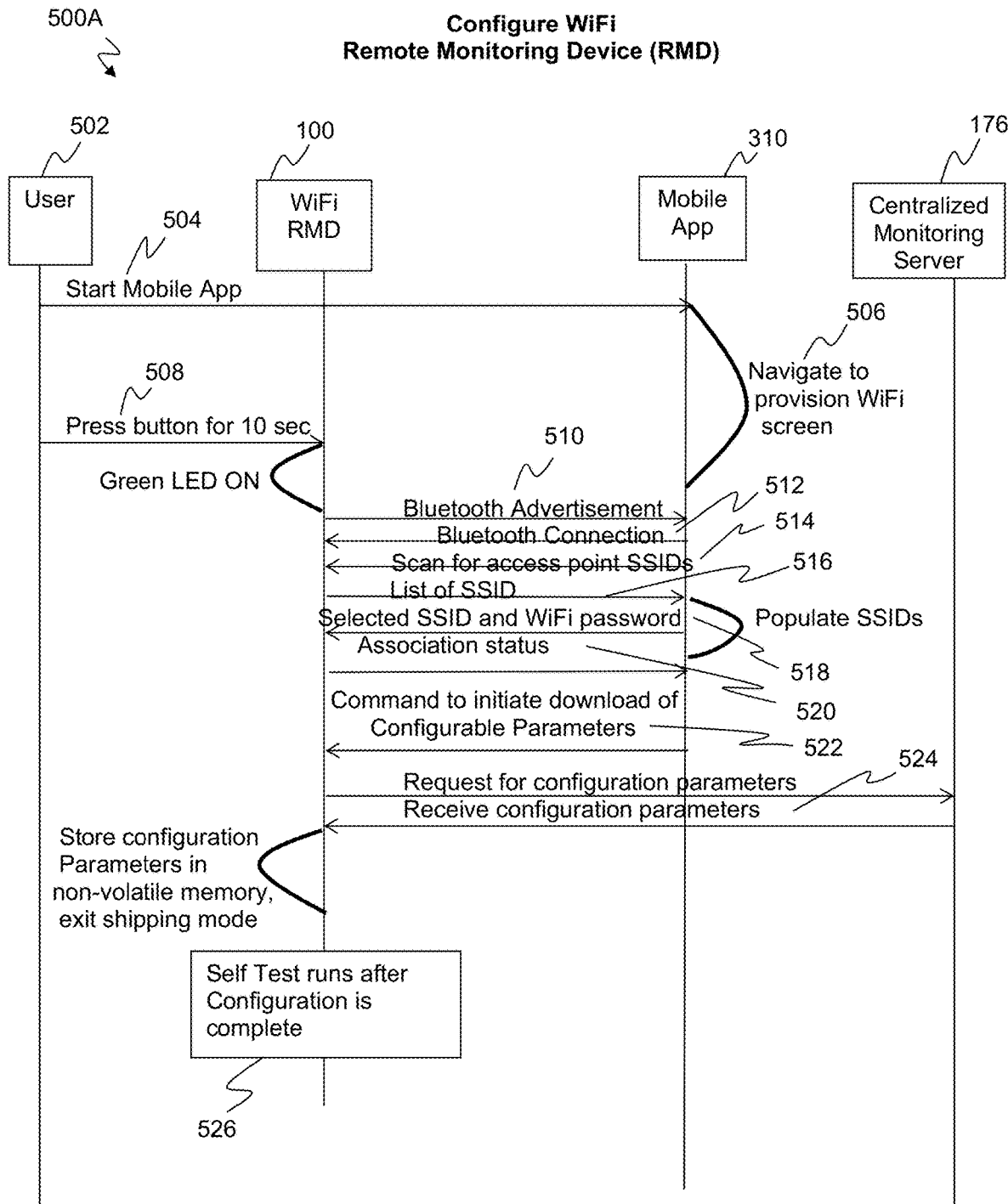
FIG. 7 is a diagram of the communications flow for a Wi-Fi module in a system for AED remote monitoring, according to an embodiment.
Figure 8:
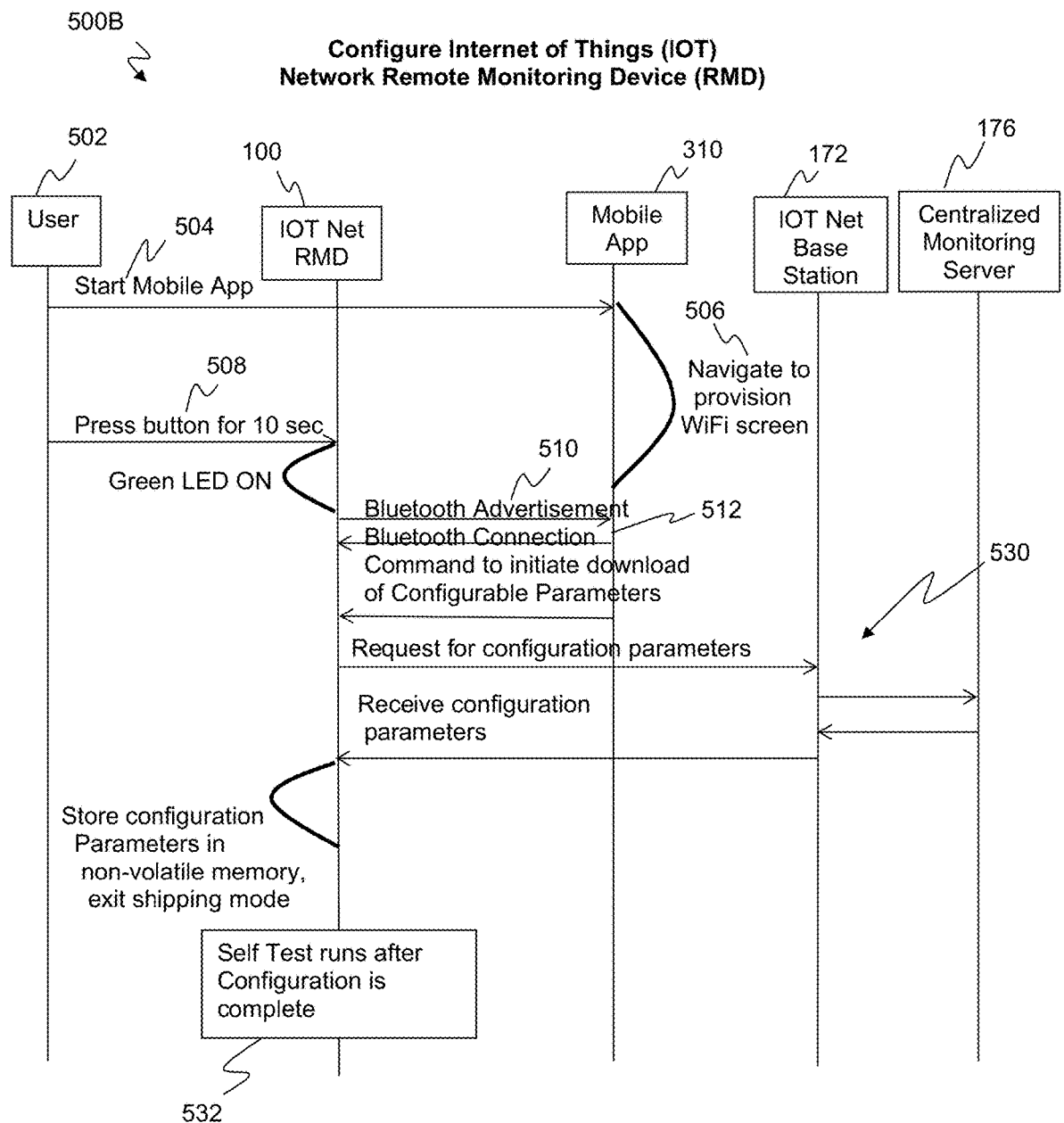
FIG. 8 is a diagram of the communications flow for a IOT network module in a system for AED remote monitoring, according to an embodiment.

FIGS. 7 and 8 show diagrams 500A and 500B of the communications flow for configuring/provisioning Wi-Fi and IOT Network remote monitoring devices 100, respectively. FIG. 7 shows a diagram of the communications flow for a Wi-Fi module 140A in a system for AED remote monitoring. As shown, a user 502, remote monitoring device 100, mobile application 310 and remote monitoring service 176 are spaced horizontally across the diagram.

As understood from FIGS. 7 and 8, provisioning remote monitoring device 100 supports firmware upgrades to the device 100, configures the remote monitoring device 100 to enable communication with the remote monitoring device server 174, enters remote monitoring device data (identification and configuration) on the centralized monitoring service 176 and, if the remote monitoring device 100 is new, adds the remote monitoring device 100 to an AED kit. The centralized monitoring service 176 may direct new data to be written into the flash memory 124 of the remote monitoring device 100.

The process begins when the user 502 turns on the mobile application 310 at 504 and navigates to the provisioning screen of the remote monitoring device 100 at 506. The user 502 also presses the button 136 on the remote monitoring device 100 for an extended period of time, such as four seconds or longer (ten seconds in some embodiments) at 508. This causes the remote monitoring device 100 to send out its Bluetooth advertisement at 510 and the mobile application 310 connects to the remote monitoring device 100 over Bluetooth at 512 and retrieves the remote monitoring device's firmware version. If the remote monitoring device firmware version is different from firmware revision available in mobile application 310, provisioning will allow remote monitoring device firmware update. If firmware update is selected, the remote monitoring device firmware will be updated. New firmware will be installed after the mobile application 310 disconnects from the remote monitoring device 100, ending the provisioning session.

At this point, two paths are possible in this embodiment: one for a Wi-Fi remote monitoring device 100 depicted in FIG. 7 and another for a IOT network remote monitoring device 100 depicted in FIG. 8. For a Wi-Fi remote monitoring device 100 in FIG. 7, the mobile application 310 commands the remote monitoring device 100 to scan for the SSIDs visible at 514 and transfers that list of SSIDs to the mobile application 310 at 516. The user 502 selects the SSID of the Wi-Fi access point and enters the password for the Wi-Fi access point at 518; the mobile application 310 passes both to the remote monitoring device 100. The remote monitoring device 100 determines if it can associate with the access point and communicates association status to the mobile application 310 at 520. Following a successful association, the remote monitoring device 100 is commanded to initiate download of parameters at 522 and communicate with the centralized monitoring service 176 to upload/download its configurable parameters at 524. Provisioning is then complete and the remote monitoring device 100 will enter self-test and begin normal operations at 526.

As shown in FIG. 8, the connection for an IOT network remote monitoring device 100 is simpler. Following Bluetooth connection, described previously, the remote monitoring device 100 is commanded to transmit and receive data over the IOT network, including the base station 172. Utilizing the IOT network, the remote monitoring device 100 communicates with the centralized monitoring service 176 to upload/download its configurable parameters at 530. Provisioning is then complete, and the remote monitoring device will enter self-test and begin normal operations at 532.

Figure 9:
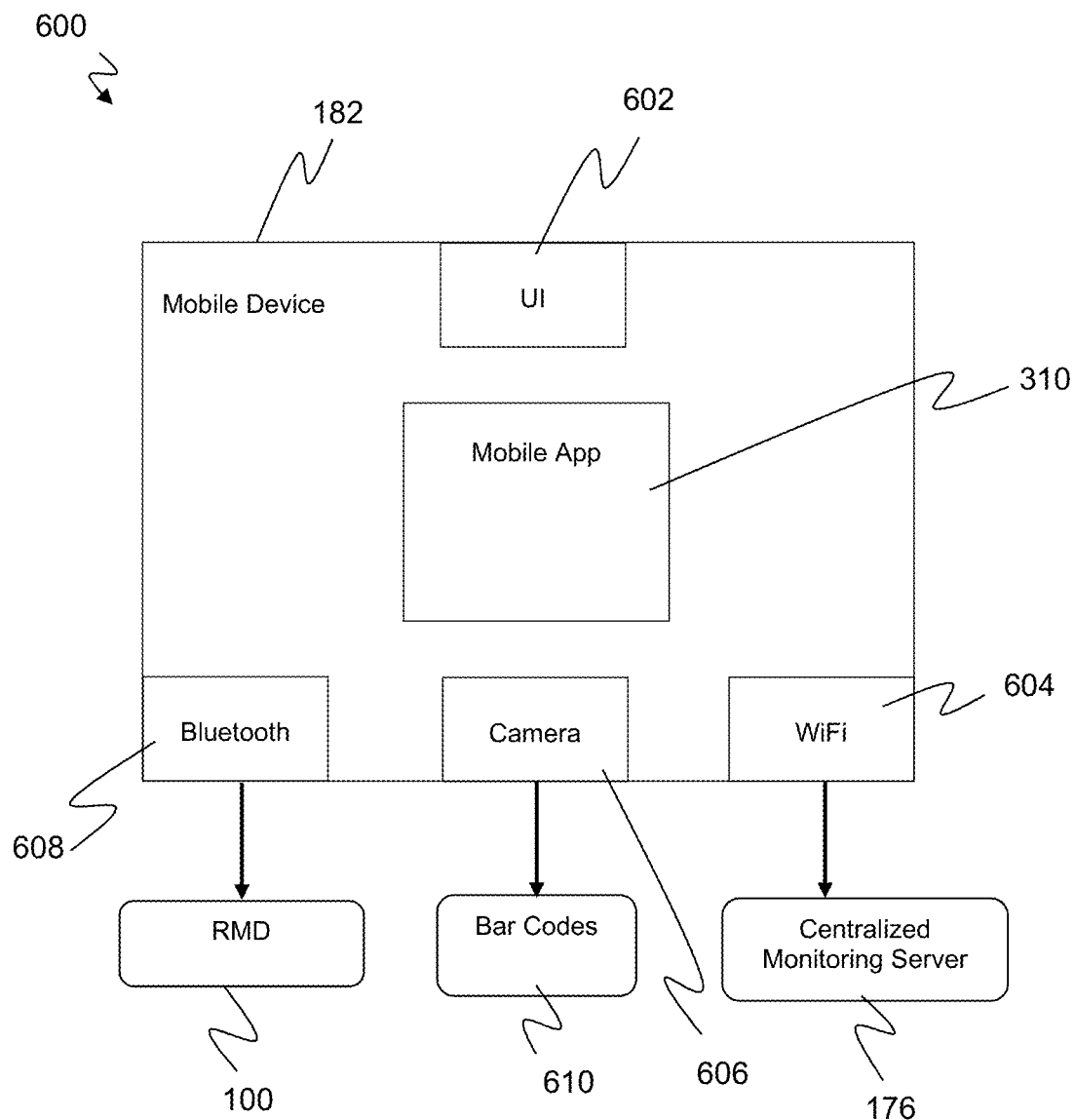
FIG. 9 is an architecture diagram of the mobile application for the remote monitoring device system, according to an embodiment.

In FIG. 9 an architecture diagram 600 of an embodiment of the mobile application 310 for the remote monitoring device system is depicted. Specifically, a mobile device 182 is shown that is running the mobile application 310. The mobile device 182 further includes: a user interface 602; Wi-Fi circuitry 604; a camera 606; and Bluetooth enabled circuitry 608. The Wi-Fi circuitry 604 (or its cellular data connection) is used to connect to the centralized monitoring service 176. The camera 606 can be used to scan information codes 610 (i.e. bar codes, QR codes, etc.) on the remote monitoring device 100 and the AED 10 so that the remote monitoring device 100 can be added to the AED kit database in the centralized monitoring service 176. Bluetooth 508 is used to connect to the remote monitoring device 100 for configuration of remote monitoring device-specific parameters as needed.

Figure 10:
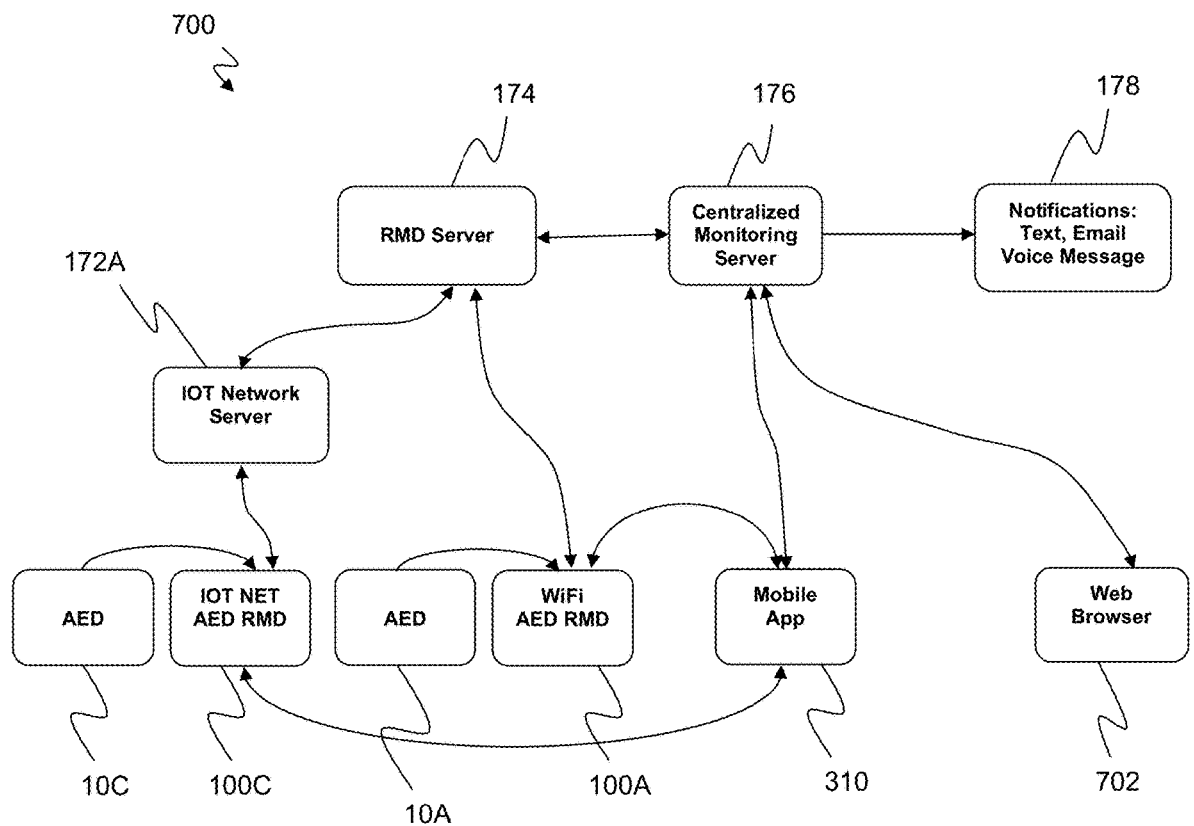
FIG. 10 shows a diagram of the data flow for a remote monitoring device system, according to an embodiment.

FIG. 10 shows a diagram 700 of the remote monitoring data flow at a high level for an embodiment of the system. As indicated, both Wi-Fi and IOT network-based AED remote monitoring devices 100 (individually referred to as remote monitoring device 100A and 100C here, respectively) have a similar high-level function. AED remote monitoring devices 100 will initiate a connection to the AED remote monitoring device server 174 if it detects an AED self-test error beep. AED remote monitoring devices 100 also check-in on a periodic basis, nominally every 24 hours.

The ultimate destination for the AED remote monitoring device data is the centralized monitoring server 176. The server 176 maintains an AED remote monitoring device's configuration, which is pushed back to the AED remote monitoring device 100 whenever the AED remote monitoring device 100 establishes a connection. The nature of the data-path and the format of the data are different between a Wi-Fi and IOT network-based AED remote monitoring devices 100, but the functions and purposes are the same.

Wi-Fi-based AED remote monitoring devices 100A will establish a logical connection (a session) directly to the AWS AED remote monitoring device server 174 and exchange JSON formatted messages. The AED remote monitoring device server 174 will exchange JSON-formatted messages to the centralized monitoring server 176. The AED remote monitoring device server 174 will receive from centralized monitoring server 176 the AED remote monitoring device's configuration which it will then send back to the AED remote monitoring device 100A.

In various embodiments, IOT network AED remote monitoring devices 100C, on the other hand, will connect to a IOT network server 172A which will subsequently establish a connection to the AED remote monitoring device server 174 to exchange JSON formatted messages. The API between the IOT network server 172A and the AED remote monitoring device server 174 is not the same as used by Wi-Fi based AED remote monitoring devices 100 primarily due to limitations imposed by the IOT network protocol. In one embodiment, the IOT network server 172A bundles the 12-byte AED remote monitoring device payload and IOT network-provided meta-data to the AED remote monitoring device server 174. The metadata contains information, such as signal strength, and which IOT network base station received the AED remote monitoring device's message. The AED remote monitoring device server 174 interprets/converts the AED remote monitoring device's 12-byte payload and exchanges JSON-formatted messages to the centralized monitoring server 176. The remote monitoring device server 174 receives the AED remote monitoring device's configuration from the centralized monitoring server 176 and reformats as necessary before sending it to the IOT network server 172A which then sends the downlink payload to the AED remote monitoring device 100.

In various embodiments, there is only one API between the AED remote monitoring device server 174 and the centralized monitoring server 176. The AED remote monitoring device server 174 also extracts and maintains a database of the IOT network metadata for future data mining projects.

In various embodiments, switching circuitry 141 as shown in FIG. 2B is included as part of the remote monitoring device 100 to enable the remote monitoring device to be more adaptable for different customer facility configurations depending, for example, on the type of Wi-Fi network (simple WPA or more complex Enterprise class networks (e.g., using high end Cisco routers)) that may be in the facilities and/or campuses of a given customer. The more complex the Wi-Fi network, the more coordination of multiple functions may need to be performed by the customer to reliably set up the remote monitoring devices 100. In these situations, the ability for the remote monitoring device 100 to selectively switch between two or more of the PAN, LAN and WAN networks, for example, can provide both a more flexible and adaptable network communication, as well as a more reliable communication network connection if one of the communication channels were to go down for any reason. In addition, this flexibility can decrease the setup complexity for complex Wi-Fi networks by using a cellular network instead. This flexibility can also reduce false alerts due to failures or power interruptions in a customer Wi-Fi access point.

In some embodiments, customers may prefer to set up all of the remote monitoring devices 100 and corresponding AEDs 10 at the same time in a central location such as a conference room. This is not recommended, since the Wi-Fi signal strength will be different at the locations where the remote monitoring devices 100 are deployed, versus in the central location. In such situations, the actual location of a given remote monitoring devices 100 and corresponding AED 10 may be manually entered into the backend server or via the mobile app, although this can be both inefficient and error prone and needs to be updated if the remote monitoring devices 100 and corresponding AED 10 is moved to a different location.

The use of a primary or switchable cellular network for communication module 142 can provide advantages of less reliance on customer support, a single consistent interface that facilitates a common area for setup. In some embodiments, a current location of the remote monitoring devices 100 and corresponding AEDs 10 can be determined through cellular triangulation techniques and that current information can be automatically determined. In other embodiments, the addition of a GPS circuitry to the remote monitoring device 100 can provide even greater resolution in helping to identify a location of the device 100 and AED 10 within a building. In these embodiments, the current location can be communicated to the server to eliminate/reduce the need to manually enter/keep track of the current location of the device 100 and AED 10. In such cellular embodiments, the data/bandwidth required can be relatively low, similar to telemetry applications, which can facilitate the use of older and cheaper WAN technologies that can have greater cellular network availability and at reduced cost compared to the latest cellular technologies such as 5G.

In some of such cellular-equipped embodiments, the remote monitoring device 100 can be configured to communicate with authorized users who are trained in AED rescues in an emergency situation. In various embodiments, these authorized users could have their location tracked based on their own cellphone, for example, such that a device 100 and AED 10 closest to the authorized user could inform it where that device 100 and AED 10 is located (either via an interface or notification on the mobile phone screen or by playing audible prompts). In other embodiments, this notification feature could be augmented with geofencing, such that given areas/regions in a building, can be associated with specific remote monitoring devices 110 corresponding AEDs 10 in relation to the authorized users within a geofenced area.

In some embodiments, a one-way PAN communication between the AED 10 and the remote monitoring devices 100 is provided to augment/overcome potential false positive alerts in loud ambient noise environments. In some embodiments, NFC communication technology in a transmit-only configuration pairs the AED 10 with the remote monitoring devices 100. Transmit-only for such NFC communication addresses any cybersecurity concerns as there would be no communication allowed into the AED 10. In embodiments, the NFC data transmitted could also be encrypted similar to NFC credit card readers to secure proprietary data being sent between the AED 10 and the remote monitoring device 100.

In various embodiments, a plurality of switchable network interfaces are provided in the remote monitoring device 100, In some embodiments, a plurality of switchable network interfaces are operably connected to switching circuitry and/or to the one or more processors. In embodiments, a seamless switching between the networks as a function of signal strength, network availability, cost, customer preference, for example. In various embodiments, a configuration for LAN and/or cellular/satellite WAN interfaces could include, for example, Wi-Fi 6, Wi-Fi 5 GHz, Wi-Fi 2.4 GHz, Cellular 3G, 4G, LTE, 5G, and LEO. Utilization of such a plurality of switchable network interfaces could improve the overall network availability and reliability for the remote monitoring device 100 and monitoring service.

In some embodiments, the remote monitoring device 100 could be provided with a port to allow for PCMCIA or SIM chip provision of a WAN communication interface to communicate with LEO satellites. Such LEO interfaces could provide coverage virtually everywhere and could provide a safety net in cases where there is no Wi-Fi and no terrestrial cellular coverage (e.g., maritime or remote environments)

A mobile device 182 running a mobile application 310 is used for provisioning and configuration of the AED remote monitoring device 100. The mobile application 310 connects to both the AED remote monitoring device 100 over a Bluetooth link and to the centralized monitoring server 176 via Wi-Fi or IOT network. The mobile application 310 interfaces with the centralized monitoring server 176 so a user can select an AED 'Kit'. In this context, an AED kit is a configuration that aggregates the AED and other elements of the system.

The mobile application 310 uses a Bluetooth link control and AED remote monitoring device 100 configuration as needed. Wi-Fi-based AED remote monitoring devices 100 require local configuration for the network ID, and security parameters. AED remote monitoring device configuration items are entered into the centralized monitoring server 176 and are ultimately downloaded by the AED remote monitoring device 100 whenever it establishes a connection to the AED remote monitoring device server 174. More specifically, the AED remote monitoring device's configuration is received from the centralized monitoring server 176 when the AED remote monitoring device server 174 sends a remote monitoring device's status to the centralized monitoring server 176. The AED remote monitoring device server 174 then sends the configuration in the reply to the AED remote monitoring device 100 via the IOT network or Wi-Fi link. Web browser 702 is present providing an API to the centralized monitoring server 176.

Some embodiments relate to a mobile device application 310 and related systems. For example, a system for AED monitoring utilizing a mobile device 182 is disclosed. The system includes a mobile application 310 and a remote management server such as centralized monitoring server 176. The mobile application 310 is configured to be executable on the mobile device 182 to receive data about an AED 10 and an AED remote monitoring device 100. The remote management server (i.e. centralized monitoring server 176) is configured to communicate with the mobile device 182 and receive data from the mobile device 182. The mobile application 310 is executable on the mobile device 182 is configured to: establish a communications connection between the mobile device 182 and the AED remote monitoring device 100; establish a communications connection between the mobile device 182 and the remote management server (i.e. centralized monitoring server 176); receive or obtain a location of at least one of the AED 10 or the AED remote monitoring device 100; use the communications connection between the mobile device 182 and the AED remote monitoring device 100 and the location to configure the AED remote monitoring device 100 with site-specific parameters; and communicate a notification 178 to the remote management server (i.e. centralized monitoring server 176) of an attempt of the AED remote monitoring device 100 to connect to the remote management server (i.e. centralized monitoring server 176).

Many embodiments are possible with respect to the various systems and methods described throughout this disclosure. In some embodiments, the mobile application 310 is further configured to communicate product data of the mobile device 182 via camera images of QR codes or barcodes 610 on the AED 10 and on the AED remote monitoring device 100 and communicate the product data to the remote management server. In some embodiments, the product data about the AED 10 includes scanned expiration dates for associated AED pads and battery. In some embodiments, the site-specific parameters include network ID and security credentials. In some embodiments, the location of at least one of the AED 10 or the AED remote monitoring device 100 is obtained from GPS coordinates of the mobile device 182. In other embodiments, the location of at least one of the AED 10 or the AED remote monitoring device 100 is obtained and is pre-programmed into memory either on the server or the mobile application. Location information may be the form of an street address. Location may also include instructions for locating a device once the person has entered an address, e.g. "first floor, to the right of the main elevator." In some embodiments, at least one of the mobile application 310 or the remote management server is further configured to check information about a last self-test failure of the AED 10 using the mobile device 182. The information can relate to one or more of: a failure type; a pad expiration details; a battery expiration; and a check of log status, for example. In some embodiments, at least one of the mobile application 310 or the remote management server is further configured to program the AED 10 with an updated configuration via the mobile device 182. In some embodiments, at least one of the mobile application 310 or the remote management server is further configured to program the AED remote monitoring device 100 via the mobile device 182. In some embodiments, the communications connection between the mobile device 182 and the AED monitoring device 100 is established via a Bluetooth link. In some embodiments, the communications connection between the AED monitoring device 100, the mobile device 182 and the remote management server is established via a Wi-Fi link or a cellular data link 313A.

Some embodiments relate to a mobile device application 310 and related methods. For example, a method for AED monitoring utilizing a mobile device 182. The method includes establishing, by a mobile application 310 configured to be executable on a mobile device 182, a communication connection between the mobile device 182 and the AED remote monitoring device 100. In embodiments, the method includes establishing, by the mobile application 310, a communications connection between the mobile device 182 and a remote management server (i.e. centralized monitoring server 176) that is configured to communicate with the mobile application 310 and receive data from the mobile device 182.

In embodiments, the method includes launching, by the remote management server, an AED kit engine upon determining that a mobile application 310 is activated on the mobile device 182. The method includes executing, by the remote management server, the AED kit engine to establish an AED kit that pairs the AED 10 and the AED remote monitoring device 100 and includes at least product data about the AED 10 and the AED remote monitoring device 100. The method includes receiving or obtaining, via at least one of the mobile application 310 or the remote management server, an AED kit location. The method includes configuring, via at least one of the mobile application 310 or the remote management server, the AED monitoring device 100 with site-specific parameters using the communications connection. The method includes communicating, via at least one of the mobile application 310 or the remote management server, a notification of an attempt of the AED monitoring device 100 to connect to the remote management server.

FIGS. 11A-C are screenshots 800A, 800B, and 800C of the interface of a mobile application 310 shown on a mobile device 182 for monitoring of AEDs 10 via remote monitoring devices 100. FIG. 11A shows an example of a particularly identified AED 10 and a status summary of items associated with the AED 10. Information 802 such as the ID number and model number of the AED 10 can be seen, as well as the lot, expiration, and type of the battery and pads. Further, the remote monitoring device 100 itself is identified at 804 and can be managed. FIG. 11B shows a screen with a manage tag option 806 and a remove tag option 808. FIG. 11C includes a pop-up request 810 for the remote monitoring device 100 to access the devices location. These types of features are useful to the provisioning process and permit quick and easy pairing of AEDs 10 and remote monitoring devices 100.

Figure 12:
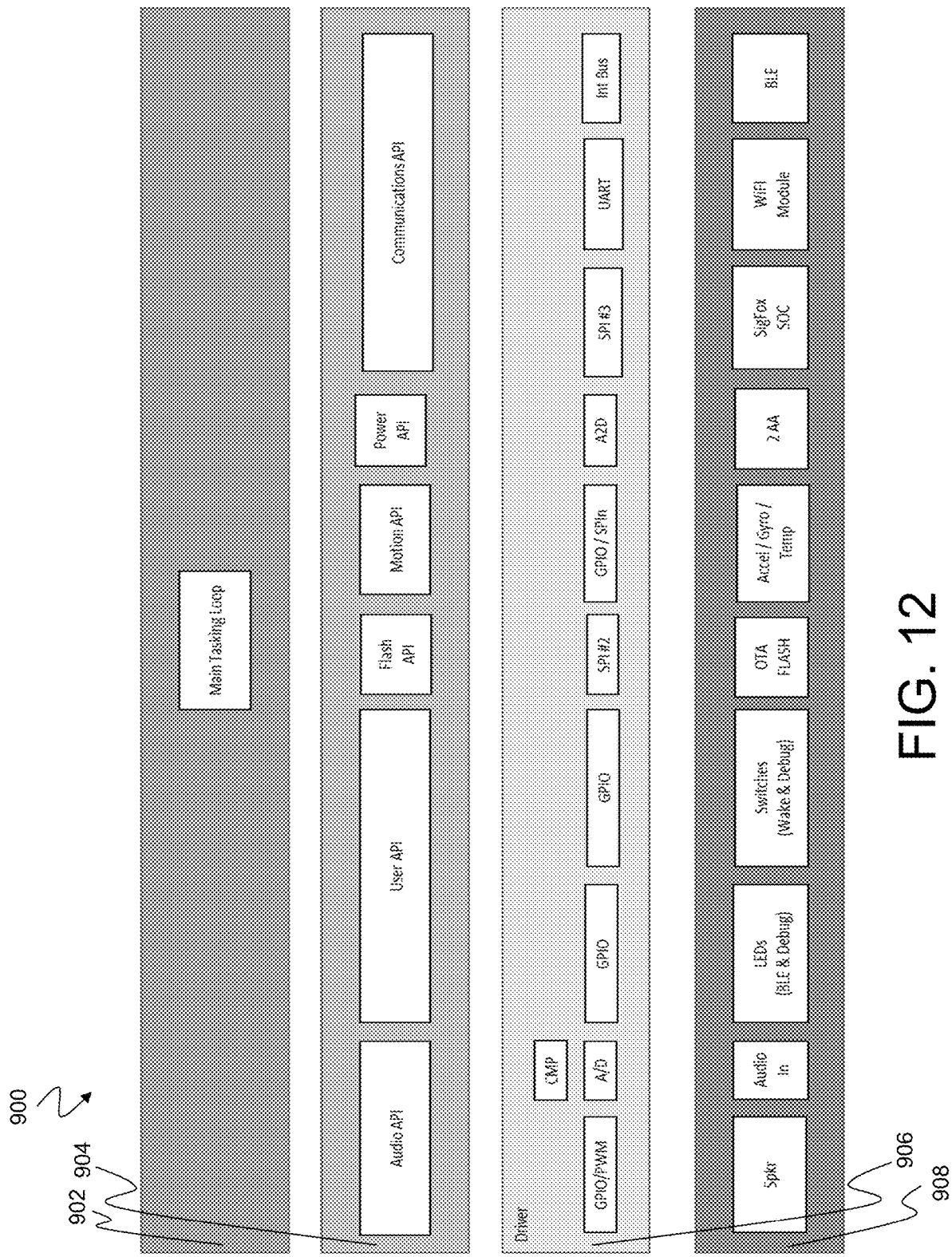
FIG. 12 is a diagram of the remote monitoring device software subsystem, according to an embodiment.

FIG. 12 is a diagram of the remote monitoring device software subsystem 900. The layers of the application include: an application layer 902; an API layer 904; a driver layer 906; and a hardware layer 908. The application layer 902 provides the main tasking loop which handles the various states and mode of the remote monitoring device 100. The API layer 904 abstracts hardware details from the tasking layer 902 by providing high-level commands and control functions but does not expose its inner workings or the details of the lower level drivers. The driver layer 906 directly interfaces to the hardware. The hardware layer 908 represents the physical chip or registers in attached peripheral devices.

In general, embodiments of the software architecture for the remote monitoring device 100 provide an event driven embedded system, main loop state machine waiting for events in low power state, and three loosely coupled subsystems. Specifically, the loosely coupled subsystems include of audio processing, a communications handler, and BLE command processing. Each subsystem processes its own events generated by interrupts or other subsystems. Functions include running to completion (no pre-emption).

In some embodiments, the remote monitoring device 100 can be understood to relate to a small battery-powered device that attaches to an AED 10. The remote monitoring device 100 can be connected to the internet via Wi-Fi and report an "I'm OK" signal to the system daily and report an error message to the system when it detects the AED's chirp which indicates a failed self-test.

In some embodiments the mobile application 310 can be understood to work with smart phones (operating on Apple iOS and Google Android OS) and other mobile device 182. The mobile application 310 can connect the remote monitoring device 100 to an AED "kit" on the centralized monitoring server 176 and provide a remote interface to both the remote monitoring device 100 and centralized monitoring server 176.

In various embodiments, IoT/system components provide a subsystem of commercial internet components of the overall system, including a remote monitoring device server 174 (AMS or equivalent that integrates Wi-Fi messages and feeds them to the centralized monitoring server 176), and any other Cloud or user-hosted systems which are required to run the overall Remote Monitor system. These components are commercial systems which use standard internet protocols, and they communicate with each other and with the centralized monitoring server 176 via Application Protocol Interfaces (APIs).

In some embodiments, the AED 10 can include embedding a signal in the audible chirp to indicate what issues the AED 10 might have, such as whether: the electrodes have expired; the electrodes are not functional; or the battery life has expired. These can be heard by the remote monitoring device 100 but would need to be decoded. This information can be valuable to the maintenance person but would not impact therapy and would not provide personal identifiable information. In various embodiments to address cyber security concerns, AED chirps can be encrypted and not decrypted until they reach a secure server.

In embodiments, remote monitoring device 100 and the related system and/or its components or systems can include computing devices, microprocessors, modules and other computer or computing devices, which can be any programmable device that accepts digital data as input, is configured to process the input according to instructions or algorithms, and provides results as outputs. In an embodiment, computing and other such devices discussed herein can be, comprise, contain or be coupled to a central processing unit (CPU) configured to carry out the instructions of a computer program. Computing and other such devices discussed herein are therefore configured to perform basic arithmetical, logical, and input/output operations.

Computing and other devices discussed herein can include memory. Memory can comprise volatile or non-volatile memory as required by the coupled computing device or processor to not only provide space to execute the instructions or algorithms, but to provide the space to store the instructions themselves. In embodiments, volatile memory can include random access memory (RAM), dynamic random access memory (DRAM), or static random access memory (SRAM), for example. In embodiments, non-volatile memory can include read-only memory, flash memory, ferroelectric RAM, hard disk, floppy disk, magnetic tape, or optical disc storage, for example. The foregoing lists in no way limit the type of memory that can be used, as these embodiments are given only by way of example and are not intended to limit the scope of the present disclosure.

In embodiments, the system or components thereof can comprise or include various modules or engines, each of which is constructed, programmed, configured, or otherwise adapted, to autonomously carry out a function or set of functions. The term "engine" as used herein is defined as a real-world device, component, or arrangement of components implemented using hardware, such as by an application-specific integrated circuit (ASIC) or field-programmable gate array (FPGA), for example, or as a combination of hardware and software, such as by a microprocessor system and a set of program instructions that adapt the engine to implement the particular functionality, which (while being executed) transform the microprocessor system into a special-purpose device. An engine can also be implemented as a combination of the two, with certain functions facilitated by hardware alone, and other functions facilitated by a combination of hardware and software. In certain implementations, at least a portion, and in some cases, all, of an engine can be executed on the processor(s) of one or more computing platforms that are made up of hardware (e.g., one or more processors, data storage devices such as memory or drive storage, input/output facilities such as network interface devices, video devices, keyboard, mouse or touchscreen devices, etc.) that execute an operating system, system programs, and application programs, while also implementing the engine using multitasking, multithreading, distributed (e.g., cluster, peer-peer, cloud, etc.) processing where appropriate, or other such techniques. Accordingly, each engine can be realized in a variety of physically realizable configurations and should generally not be limited to any particular implementation exemplified herein, unless such limitations are expressly called out. In addition, an engine can itself be composed of more than one sub-engines, each of which can be regarded as an engine in its own right. Moreover, in the embodiments described herein, each of the various engines corresponds to a defined autonomous functionality; however, it should be understood that in other contemplated embodiments, each functionality can be distributed to more than one engine. Likewise, in other contemplated embodiments, multiple defined functionalities may be implemented by a single engine that performs those multiple functions, possibly alongside other functions, or distributed differently among a set of engines than specifically illustrated in the examples herein.

Various embodiments of systems, devices, and methods have been described herein. These embodiments are given only by way of example and are not intended to limit the scope of the present disclosure. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the present disclosure.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art.

Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. A remote monitoring device for monitoring and managing by a monitoring service via a communications network a condition of an automated external defibrillator (AED) based on audio signals from the AED, comprising:
   a housing configured to be positioned outside of the AED such that audio sounds from the AED can be detected, the housing containing:
     at least one processor;
     a communications module operably connected to the at least one processor and configured to transmit electronic communications to the monitoring service via the communications network;
     at least one audio sensor;
     at least one audio detection circuitry operably connected to one or more of the at least one audio sensor and the at least one processor, the at least one audio detection circuitry configured to:
       generate a notification signal when detecting audio sounds during a predetermined detection interval, and
       commence an active listening mode to provide digital audio signals to the at least one processor in response to the notification signal,
     wherein the at least one processor is configured to power on in response to the notification signal, process the digital audio signals, and transmit a signal to the monitoring service to report a condition of the AED based on the digital audio signals that are processed.

2. The remote monitoring device of claim 1, wherein the at least one processor is configured to transmit the signal to a centralized monitoring service or server with a database.

3. The remote monitoring device of claim 1, wherein the at least one processor is further configured to power down once it transmits the signal to the monitoring service.

4. The remote monitoring device of claim 1, wherein the at least one audio sensor includes an analog microphone that detects audio sounds based on sound amplitude.

5. The remote monitoring device of claim 1, wherein the communications module is configured to wirelessly transmit electronic communications.

6. The remote monitoring device of claim 5, wherein the communications module utilizes one of a Wi-Fi or IOT network to wirelessly transmit electronic communications.

7. The remote monitoring device of claim 1, wherein the signal transmitted to the monitoring service identifies a serial number of the AED.

8. The remote monitoring device of claim 1, wherein the audio sounds from the AED include information based on an encoding scheme, and wherein the at least one processor is configured to analyze the processed signals from the at least one audio detection circuitry to cause the signal transmitted to the monitoring service to include status information of the AED based on the encoding scheme.

9. The remote monitoring device of claim 1, wherein the audio sounds from the AED communicate at least one of the following: a self-test failure of the AED; a battery expiration; and an electrode expiration.

10. The remote monitoring device of claim 1, wherein increases in an amplitude of the audio sounds from the AED are used to convey a level of urgency in the signal.

11. The remote monitoring device of claim 1, wherein the audio sounds from the AED include at least one of variations in inter-tone timing and length to convey information as part of the signal.

12. The remote monitoring device of claim 1, further comprising an optical sensor operably connected to the at least one processor to detect whether the AED presents a visual indication of an AED self-test failure.

13. The remote monitoring device of claim 8, wherein the encoding scheme is a frequency shift keying technique.

14. The remote monitoring device of claim 1, wherein the at least one audio detection circuitry is configured to power on during the predetermined detection interval.

15. The remote monitoring device of claim 1, wherein the at least one processor is configured to power down if any of these conditions are not met: a first qualifying tone is not detected in the digital audio signals during a first active listening interval; a second qualifying tone is not detected in the digital audio signals during a second active listening interval; or a third qualifying tone is not detected in the digital audio signals during a third active listening interval.

16. A remote monitoring device for monitoring audio signals from an automated external defibrillator (AED) and electronically reporting to a monitoring service via a communications network, comprising:
a housing configured to be positioned outside of the AED such that audio signals from the AED can be detected, the housing containing:
at least one processor;
a memory operably connected to the at least one processor;
a communications module operably connected to the at least one processor and configured to transmit electronic communications to the monitoring service via the communications network;
a speaker operably connected to the at least one processor and configured to generate audio sounds as part of a self-test of the remote monitoring device;
at least one audio sensor; and
at least one audio detection circuitry operably coupled with the at least one audio sensor, the at least one audio detection circuitry configured to detect audio sounds via the at least one audio sensor and provide digital audio signals to the at least one processor,
wherein the at least one processor is configured to:
periodically cause the speaker to generate the audio sounds as part of the self-test of the remote monitoring device,
receive the digital audio signals to confirm that the audio sounds as part of the self-test of the remote monitoring device originate from the speaker, and
transmit a message conveying results of the self-test of the remote monitoring device to the monitoring service via the communications network.

17. The remote monitoring device of claim 16, wherein the speaker is a piezo-speaker.

18. The remote monitoring device of claim 16, wherein the at least one audio detection circuitry is configured to power on during an analog detection interval and generate a wakeup notification signal when audio sounds are detected during the analog detection interval.

19. The remote monitoring device of claim 18, wherein the at least one audio detection circuitry is configured to power on in response to the wakeup notification signal and commence an active listening mode.

20. The remote monitoring device of claim 16, wherein the housing includes a battery of indeterminate life operably connected to the at least one processor and the communications module.

21. The remote monitoring device of claim 20, wherein the self-test is further configured to measure a battery voltage of the battery under load during at least two successive transmissions by the communications module to determine if a low battery status is present.

22. The remote monitoring device of claim 16, wherein the at least one processor causes the communications module to provide information related to battery status from a previous transmission.

23. The remote monitoring device of claim 16, wherein the self-test is configured to be conducted daily in response to one of a 24-hour timer or on any physical button presses of the remote monitoring device.

24. The remote monitoring device of claim 16, wherein the communications module is configured to wirelessly transmit electronic communications.

25. The remote monitoring device of claim 24, wherein the communications module utilizes a Wi-Fi or IOT network for wireless electronic communications.

* * * * *